US012226159B2

(12) United States Patent
Ashok et al.

(10) Patent No.: US 12,226,159 B2
(45) Date of Patent: Feb. 18, 2025

(54) VOLUMETRIC OCT IMAGE DATA PROCESSING

(71) Applicant: OPTOS PLC, Dunfermline (GB)

(72) Inventors: Praveen Ashok, Dunfermline (GB); Alan Anderson, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 692 days.

(21) Appl. No.: 17/492,592

(22) Filed: Oct. 2, 2021

(65) Prior Publication Data

US 2022/0142472 A1   May 12, 2022

(30) Foreign Application Priority Data

Nov. 12, 2020 (EP) .................................. 20207149

(51) Int. Cl.
*A61B 3/10* (2006.01)
*A61B 5/00* (2006.01)
*G16H 30/40* (2018.01)

(52) U.S. Cl.
CPC ............ *A61B 3/102* (2013.01); *A61B 5/7221* (2013.01); *G16H 30/40* (2018.01)

(58) Field of Classification Search
CPC ..... A61B 3/102; A61B 3/1225; A61B 5/7221; G16H 30/40
See application file for complete search history.

(56) References Cited

U.S. PATENT DOCUMENTS 7,997,729 B2   8/2011   McLean et al.
9,759,544 B2   9/2017   An et al.
2011/0267340 A1  11/2011   Kraus et al.
(Continued)

FOREIGN PATENT DOCUMENTS

| CN | 103025229 A | 4/2013 |
|----|-------------|--------|
| CN | 105942968 A | 9/2016 |

(Continued)

OTHER PUBLICATIONS

Chen et al., "Repeatability of spectral domain OCT in measuring retinal nerve fiber layer thickness at different scanning radii", Journal of Shantou University Medical College, vol. 1, No. 1, 2019.
Zhang et al., "Methods and algorithms for optical coherence tomography-based angiography: a review and comparison", Journal of Biomedical Optics, vol. 20, No. 10, Oct. 2015, pp. 1-14.
Decision to Grant a Patent, issued Jul. 4, 2022 in Japanese Patent Application 2021-180140 (1 sheet); English translation attached (2 sheets).

(Continued)

*Primary Examiner* — Jack Dinh
(74) *Attorney, Agent, or Firm* — FAEGRE DRINKER BIDDLE & REATH

(57) ABSTRACT

A method of processing B-scans acquired by an OCT imaging system to generate correction data for compensating for axial displacements between B-scans caused by a variation in distance between the OCT imaging system and an imaging target, and to generate a reliability indicator indicative of a reliability of the correction data. The correction data is generated by determining, for each pair of adjacent B-scans, a respective indicator of an axial shift between respective representations of a common ocular feature in the adjacent B-scans. The reliability indicator is generated by: calculating values indicative of speeds or accelerations of the imaging target relative to the OCT imaging system when pairs of B-scans were acquired; where at least a predetermined number of calculated values exceed a threshold, setting the reliability indictor to indicate that the correction data is unreliable, and otherwise to indicate that the correction data is reliable.

20 Claims, 13 Drawing Sheets

(56) References Cited

U.S. PATENT DOCUMENTS

| | | | |
|---|---|---|---|
| 2012/0075640 | A1 | 3/2012 | Sakagawa et al. |
| 2014/0211155 | A1 | 7/2014 | Sakagawa et al. |
| 2016/0040977 | A1 | 2/2016 | An et al. |
| 2017/0020387 | A1 | 1/2017 | Fingler et al. |
| 2017/0258317 | A1 | 9/2017 | Bajraszewski et al. |
| 2019/0278972 | A1 | 9/2019 | Anderson et al. |
| 2019/0347774 | A1 | 11/2019 | Fleming et al. |
| 2020/0320754 | A1 | 10/2020 | Ashock et al. |

FOREIGN PATENT DOCUMENTS

| | | |
|---|---|---|
| CN | 107212852 A | 9/2017 |
| CN | 109936995 A | 6/2019 |
| CN | 110033496 A | 7/2019 |
| CN | 110473265 A | 11/2019 |
| JP | 201119576 | 2/2011 |
| JP | 2016182340 | 10/2016 |
| JP | 2017159034 | 9/2017 |

OTHER PUBLICATIONS

A. Podoleanu et al., Combinations of Techniques in Imaging the Retina with High Resolution, Progress in Retinal and Eye Research 27, No. 4 (2008), pp. 464-499.

Lingjiao Pan et al., Segmentation Guided Registration for 3D Spectral-Domain Optical Coherence Tomography Images, IEEE Access vol. 7, pp. 138833-138845 (2019).

A. Zhang et al., Methods and algorithms for optical coherence tomography-based angiography: a review and comparison, Journal of Biomedical Optics 20(10), SPIE, pp. 100901-1 to 100901-13 (Oct. 2015).

European Search Report issued on May 3, 2021 in European Patent Application No. 20 207 149.4.

Zang et al., Automated three-dimensional registration and volume rebuilding for wide-field angiographic and structural optical coherence tomography, Journal of Biomedical Optics 22(2), SPIE, pp. 026001-1 to 026001-10 (2017).

Guozhong Liu et al., Stripe motion artifact suppression in phase-resolved OCT blood flow images of the human eye based on the frequency rejection filter, Chinese Optics Letters, vol. 11, No. 3, Feb. 6, 2013 (Feb. 6, 2013), pp. 031701-1 to 031701-5.

VOLUMETRIC OCT IMAGE DATA PROCESSING

This application claims the benefit of priority based on European Patent Application EP 20 207 149.4 filed Nov. 12, 2020, which is incorporated by reference herein in its entirety, as if set forth fully herein.

TECHNICAL FIELD

Example aspects herein generally relate to the field of ophthalmic optical coherence tomography (OCT) imaging systems and, more particularly, a method and apparatus for processing C-scan data comprising a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system.

BACKGROUND

The acquisition of a typical volumetric Optical Coherence Tomography (OCT) scan (also referred to as a C-scan) of a part of a subject's eye, such as the retina, can take approximately 1 to 5 seconds. During this time, an OCT beam is repeatedly scanned by the OCT imaging system in a first scan direction to record a sequence of (two-dimensional) B-scans, each of which comprises a series of axial scans (A-scans) that are recorded at respective points on the surface of the retina along the first scan direction. The B-scans in the sequence of B-scans are normally arrayed in a direction perpendicular to the first direction. During the acquisition of a C-scan, the eye might move axially (along the direction of the OCT beam), usually due to involuntary movements of the subject. For successful rendering of a C-scan image, and to ensure accuracy of subsequent measurements performed on the basis of the C-scan image, it may be necessary to correct for motion artefacts that are caused by the motion of the subject during the capture of the C-scan. If compensation is not performed on B-scan data to correct for an axial shift between some B-scans, which is caused by the motion of subject, then the accuracy of retinal layer identification and subsequent diagnostic measurements may be adversely affected.

SUMMARY

The present inventors have devised, in accordance with a first example aspect herein, a method of processing C-scan data comprising a sequence of B-scans of an imaging target, which has been acquired by an OCT imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, and to further generate a reliability indicator which indicates a reliability of the generated correction data. The method comprises generating the correction data by determining, for each pair of adjacent B-scans of a plurality of pairs of adjacent B-scans in the sequence, a respective indicator of an axial shift between respective representations of a common ocular feature in the adjacent B-scans. The method further comprises generating the reliability indicator by: calculating, using pairs of B-scans in the sequence of B-scans, respective values of a metric which are indicative of respective speeds or respective accelerations of the imaging target relative to the OCT imaging system when the pairs of B-scans were acquired; determining if at least a predetermined number of the calculated values of the metric exceed a threshold value; in a case where at least the predetermined number of calculated values of the metric are determined to exceed the threshold value, setting the reliability indictor to indicate that the correction data is unreliable; and in a case where at least the predetermined number of calculated values of the metric are determined to not exceed the threshold value, setting the reliability indictor to indicate that the correction data is reliable.

The correction data may be generated by determining, from a variation of the determined indicators with locations of the corresponding pairs of adjacent B-scans in the sequence, a first frequency component of the variation which is indicative of the relative motion of the OCT imaging system and the imaging target during acquisition of the B-scans by the OCT imaging system.

The respective indicator of the axial shift may be determined for each pair of the adjacent B-scans by calculating a cross-correlation between the pair of adjacent B-scans and determining, as the indicator, an offset between the B-scans corresponding to a peak in the calculated cross-correlation, or by identifying respective locations of the common ocular feature in the B-scans of the pair of adjacent B-scans, and determining a displacement between the identified locations along an axis of the B-scans that is representative of an axial direction of the imaging system.

The imaging target may have a curvature, and the method may further comprise determining a second frequency component of the variation, which is indicative of the curvature of the imaging target. The second frequency component may be determined by fitting an $m^{th}$ order polynomial to the variation of the determined indicators, and the first frequency component may be determined by subtracting values of the $m^{th}$ order polynomial from the indicators in the variation of the determined indicators to generate a corrected variation of the indicators, and fitting an $n^{th}$ order polynomial to the corrected variation of the indicators, wherein m and n are integers and m is smaller than n.

The method may further comprise, in the case where reliability indicator has been set to indicate that the correction data is reliable, using the correction data to compensate for the axial displacements between the B-scans in the sequence of B-scans caused by the relative motion of the OCT imaging system and the imaging target.

In an embodiment of the first example aspect, the first frequency component may be determined by further performing at least two iterations of a process comprising steps of:

(i) calculating a plurality of residual values, each residual value being calculated as a difference between an indicator in a variation of indicators and a corresponding value of an $n^{th}$ order polynomial;

(ii) determining whether the plurality of residual values comprise an outlier value which is higher than a first positive threshold value or lower than a first negative threshold value;

(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the first frequency component and ending the process; and (iv) fitting the $n^{th}$ order polynomial to the updated variation of indicators, wherein each residual value in the plurality of residual values is calculated in the first iteration of the process as a difference between an indicator in the corrected variation of the indicators and a corresponding value of the $n^{th}$ order polynomial fitted to the corrected variation of the indicators, and wherein each residual value in the plurality of residual values is calculated in each iteration of remaining one or more iterations of the process as a difference between an indicator in the updated variation of indicators generated in a previous iteration of the process and a corresponding value of the nth order polynomial fitted to the updated variation of indicators generated in the previous iteration of the process.

In the embodiment of the first example aspect, the method may further comprise, where reliability indicator has been set to indicate that the correction data is reliable: determining a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value; in a case where the determined number of residual values is smaller than a third threshold value, compensating for the axial displacements between the B-scans in the sequence of B-scans, by applying offsets based on the first frequency component to B-scans in the sequence of B-scans; and in a case where the determined number of residual values is not smaller than a third threshold value, determining not to compensate for the axial displacements between the B-scans in the sequence of B-scans.

Furthermore, the present inventors have devised, in accordance with a second example aspect herein, a method of processing C-scan data comprising a sequence of B-scans of an imaging target, which has been acquired by an OCT imaging system scanning along corresponding scan lines that extend across the imaging target, and trace scan data, which has been acquired by the OCT imaging system performing a scan along a trace scan line which crosses the scan lines, to generate correction data for compensating for axial displacements between B-scans in the sequence of B-scans caused by a relative motion of the OCT imaging system and the imaging target that varies a distance therebetween during acquisition of the B-scans by the OCT imaging system, and to further generate a reliability indicator which indicates a reliability of the generated correction data. The method comprises: generating the correction data by determining, for each B-scan of at least some of the B-scans in the sequence, a respective indicator of an axial shift between respective representations of a common ocular feature in the B-scan and trace scan data. The method further comprises generating the reliability indicator by: calculating, using the indicators determined for pairs of B-scans in the at least some of the B-scans, respective values of a metric which are indicative of respective speeds or respective accelerations of the imaging target relative to the OCT imaging system when the pairs of B-scans were acquired; determining if at least a predetermined number of the calculated values of the metric exceed a threshold value; in a case where at least the predetermined number of calculated values of the metric are determined to exceed the threshold value, setting the reliability indictor to indicate that the correction data is unreliable; and in a case where at least the predetermined number of calculated values of the metric are determined to not exceed the threshold value, setting the reliability indictor to indicate that the correction data is reliable.

The method of the second example aspect may further comprise, in the case where the reliability indicator has been set to indicate that the correction data is reliable, using the correction data to compensate for the axial displacements between the B-scans in the sequence of B-scans caused by the relative motion of the OCT imaging system and the imaging target. Additionally or alternatively, in an embodiment of the second example aspect, the correction data may be generated by performing at least two iterations of a process comprising steps of:

(i) calculating a plurality of residual values, each residual value being calculated as a difference between an indicator in a variation of indicators and a corresponding value of an $n^{th}$ order polynomial;

(ii) determining whether the plurality of residual values comprise an outlier value which is higher than a first positive threshold value or lower than a first negative threshold value;

(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the correction data and ending the process; and (iv) fitting the $n^{th}$ order polynomial to the updated variation of indicators, wherein each residual value in the plurality of residual values is calculated in the first iteration of the process as a difference between an indicator in the corrected variation of the indicators and a corresponding value of the $n^{th}$ order polynomial fitted to the corrected variation of the indicators, and wherein each residual value in the plurality of residual values is calculated in each iteration of remaining one or more iterations of the process as a difference between an indicator in the updated variation of indicators generated in a previous iteration of the process and a corresponding value of the nth order polynomial fitted to the updated variation of indicators generated in the previous iteration of the process.

In the embodiment of the second example aspect, the method may further comprise, in the case where reliability indicator has been set to indicate that the correction data is reliable: determining a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value; in a case where the determined number of residual values is smaller than a third threshold value, compensating for the axial displacements between the B-scans in the sequence of B-scans, by applying offsets based on the correction data to B-scans in the sequence of B-scans; and in a case where the determined number of residual values is not smaller than a third threshold value, determining not to compensate for the axial displacements between the B-scans in the sequence of B-scans.

Furthermore, the present inventors have devised, in accordance with a third example aspect herein, a computer program comprising computer program instructions which, when executed by a processor, cause the processor to execute at least one of the methods set out above. The computer program may be stored on a non-transitory computer-readable storage medium, or it may be carried by a signal.

Furthermore, the present inventors have devised, in accordance with a fourth example aspect herein, a data processing apparatus arranged to process C-scan data comprising a sequence of B-scans of an imaging target, which has been acquired by an OCT imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, and to further generate a reliability indicator which indicates a reliability of the generated correction data. The apparatus comprises a correction data generator module arranged to determine the correction data by determining, for each pair of adjacent B-scans of a plurality of pairs of adjacent B-scans in the sequence, a respective indicator of an axial shift between respective representations of a common ocular feature in the adjacent B-scans. The apparatus further comprises a reliability indicator generator module arranged to generate the reliability indicator by calculating, using pairs of B-scans in the sequence of B-scans, respective values of a metric which are indicative of respective speeds or respective accelerations of the imaging target relative to the OCT imaging system when the pairs of B-scans were acquired; determining if at least a predetermined number of the calculated values of the metric exceed a threshold value; in a case where at least the predetermined number of calculated values of the metric are determined to exceed the threshold value, setting the reliability indictor to indicate that the correction data is unreliable; and in a case where at least the predetermined number of calculated values of the metric are determined to not exceed the threshold value, setting the reliability indictor to indicate that the correction data is reliable.

The correction data generator module may be arranged to generate the correction data by further determining, from a variation of the determined indicators with locations of the corresponding pairs of adjacent B-scans in the sequence, a first frequency component of the variation which is indicative of the relative motion of the OCT imaging system and the imaging target during acquisition of the B-scans by the OCT imaging system.

The correction data generator module may be arranged to determine the respective indicator of the axial shift for each pair of the adjacent B-scans by calculating a cross-correlation between the pair of adjacent B-scans and determining, as the indicator, an offset between the B-scans corresponding to a peak in the calculated cross-correlation, or by identifying respective locations of the common ocular feature in the B-scans of the pair of adjacent B-scans, and determining a displacement between the identified locations along an axis of the B-scans that is representative of an axial direction of the imaging system.

The imaging target may have a curvature, and the correction data generator module may be further arranged to determine a second frequency component of the variation which is indicative of the curvature of the imaging target. The correction data generator module may be arranged to determine the second frequency component by fitting an $m^{th}$ order polynomial to the variation of the determined indicators, and determine the first frequency component by subtracting values of the $m^{th}$ order polynomial from the indicators in the variation of the determined indicators to generate a corrected variation of the indicators, and fitting an $n^{th}$ order polynomial to the corrected variation of the indicators, wherein m and n are integers and m is smaller than n.

The data processing apparatus set out above may further comprise a displacement compensation module arranged to use the correction data, in the case where the reliability indicator has been set to indicate that the correction data is reliable, to compensate for the axial displacements between the B-scans in the sequence of B-scans caused by the relative motion of the OCT imaging system and the imaging target.

In an embodiment of the fourth example aspect, the correction data generator module may be arranged to determine the first frequency component by further performing at least two iterations of a process comprising steps of:

(i) calculating a plurality of residual values, each residual value being calculated as a difference between an indicator in a variation of indicators and a corresponding value of an $n^{th}$ order polynomial;

(ii) determining whether the plurality of residual values comprise an outlier value which is higher than a first positive threshold value or lower than a first negative threshold value;

(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the first frequency component and ending the process; and (iv) fitting the $n^{th}$ order polynomial to the updated variation of indicators, wherein each residual value in the plurality of residual values is calculated in the first iteration of the process as a difference between an indicator in the corrected variation of the indicators and a corresponding value of the $n^{th}$ order polynomial fitted to the corrected variation of the indicators, and wherein each residual value in the plurality of residual values is calculated in each iteration of remaining one or more iterations of the process as a difference between an indicator in the updated variation of indicators generated in a previous iteration of the process and a corresponding value of the $n^{th}$ order polynomial fitted to the updated variation of indicators generated in the previous iteration of the process.

In the embodiment of the fourth example aspect, in the case where reliability indicator has been set to indicate that the correction data is reliable, the correction data generator module (2) may be further arranged to: determine a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value; in a case where the determined number of residual values is smaller than a third threshold value, the displacement compensation module may be arranged to compensate for the axial displacements between the B-scans in the sequence of B-scans, by applying offsets based on the correction data to B-scans in the sequence of B-scans; and in a case where the determined number of residual values is not smaller than a third threshold value, the displacement compensation module may be arranged to not to compensate for the axial displacements between the B-scans in the sequence of B-scans.

Furthermore, the present inventors have devised, in accordance with a fifth example aspect herein, a data processing apparatus arranged to process C-scan data comprising a sequence of B-scans of an imaging target, which has been acquired by an OCT imaging system scanning along corresponding scan lines that extend across the imaging target, and trace scan data, which has been acquired by the OCT imaging system performing a scan along a trace scan line which crosses the scan lines, to generate correction data for compensating for axial displacements between B-scans in the sequence of B-scans caused by a relative motion of the OCT imaging system and the imaging target that varies a distance therebetween during acquisition of the B-scans by the OCT imaging system, and to further generate a reliability indicator which indicates a reliability of the generated correction data. The apparatus comprises a correction data generator module arranged to generate the correction data by determining, for each B-scan of at least some of the B-scans in the sequence, a respective indicator of an axial shift between respective representations of a common ocular feature in the B-scan and the trace scan data. The apparatus further comprises a reliability indicator generator module arranged to generate the reliability indicator by: calculating, using the indicators determined for pairs of B-scans in the at least some of the B-scans, respective values of a metric which are indicative of respective speeds or respective accelerations of the imaging target relative to the OCT imaging system when the pairs of B-scans were acquired; determining if at least a predetermined number of the calculated values of the metric exceed a threshold value; in a case where at least the predetermined number of calculated values of the metric are determined to exceed the threshold value, setting the reliability indictor to indicate that the correction data is unreliable; and in a case where at least the predetermined number of calculated values of the metric are determined to not exceed the threshold value, setting the reliability indictor to indicate that the correction data is reliable.

The data processing apparatus of the fifth example aspect may further comprise a displacement compensation module arranged to use the correction data, in the case where the reliability indicator has been set to indicate that the correction data is reliable, to compensate for the axial displacements between the B-scans in the sequence of B-scans caused by the relative motion of the OCT imaging system and the imaging target.

In an embodiment of the fifth example aspect, the correction data generator module may be arranged to generate the correction data by performing at least two iterations of a process comprising steps of:
(i) calculating a plurality of residual values, each residual value being calculated as a difference between an indicator in a variation of indicators and a corresponding value of an nth order polynomial;
(ii) determining whether the plurality of residual values comprise an outlier value which is higher than a first positive threshold value or lower than a first negative threshold value;
(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the correction data and ending the process; and
(iv) fitting the $n^{th}$ order polynomial to the updated variation of indicators, wherein each residual value in the plurality of residual values is calculated in the first iteration of the process as a difference between an indicator in the corrected variation of the indicators and a corresponding value of the nth order polynomial fitted to the corrected variation of the indicators, and wherein each residual value in the plurality of residual values is calculated in each iteration of remaining one or more iterations of the process as a difference between an indicator in the updated variation of indicators generated in a previous iteration of the process and a corresponding value of the nth order polynomial fitted to the updated variation of indicators generated in the previous iteration of the process.

In the embodiment of the fifth example aspect, in the case where reliability indicator has been set to indicate that the correction data is reliable, the correction data generator module may be arranged to: determine a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value; in a case where the determined number of residual values is smaller than a third threshold value, the displacement compensator module is arranged to compensate for the axial displacements between the B-scans in the sequence of B-scans by applying offsets based on the correction data to B-scans in the sequence of B-scans; and in a case where the determined number of residual values is not smaller than a third threshold value, the displacement compensation module is arranged to not to compensate for the axial displacements between the B-scans in the sequence of B-scans.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

Example Embodiment 1

Figure 1:
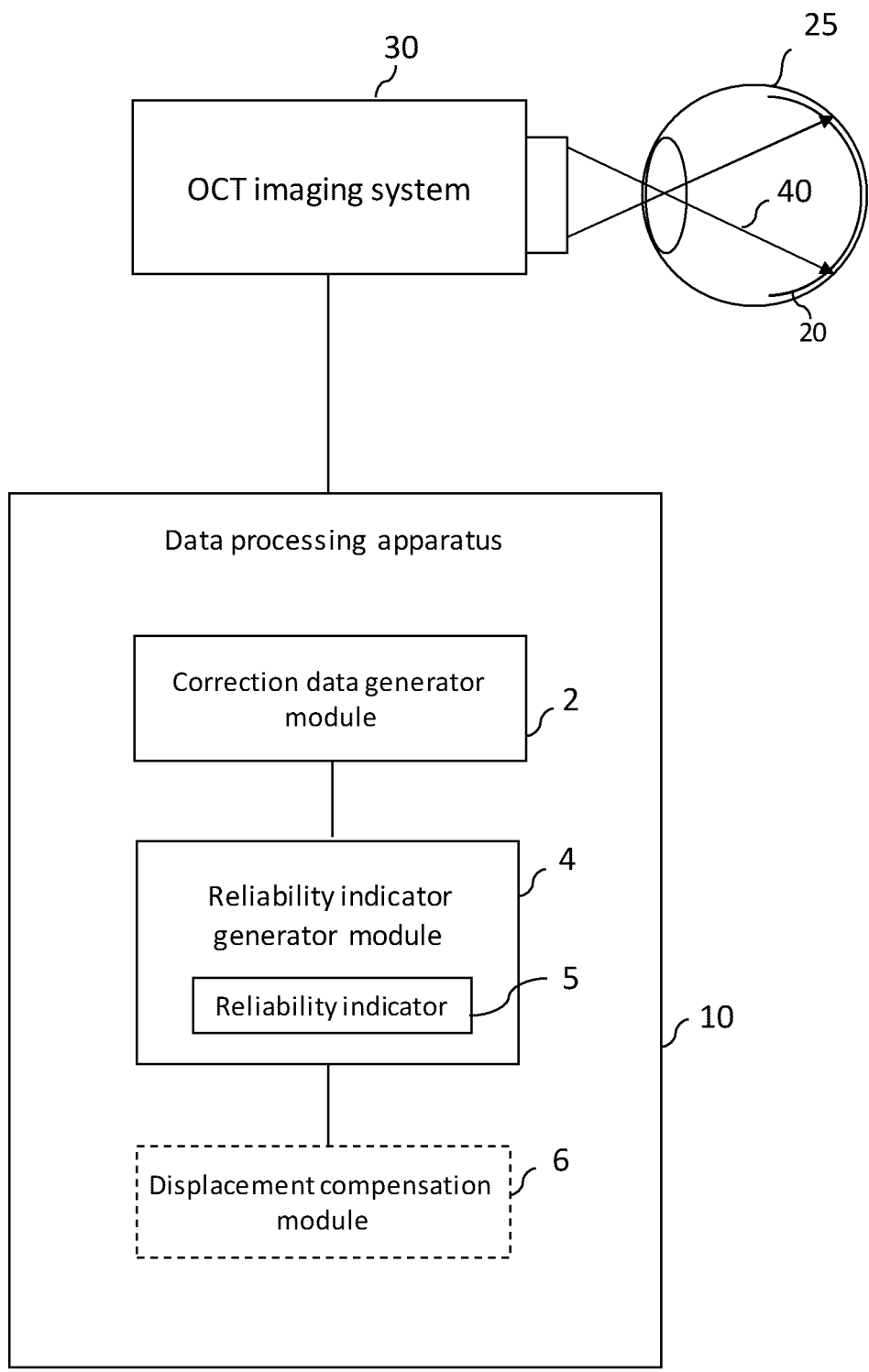
FIG. 1 is a schematic illustration of a data processing apparatus for processing C-scan data according to a first example embodiment herein.

FIG. 1 is a schematic illustration of a data processing apparatus 10 according to a first example embodiment. The data processing apparatus 10 is configured to process C-scan data comprising a sequence of B-scans of an imaging target 20, which has been acquired by an OCT imaging system 30, to generate correction data for compensating for axial displacements between B-scans in the sequence of B-scans, and to further generate a reliability indicator 5, which is indicative of the reliability of the generated correction data.

The imaging target 20 may, as in the present example embodiment, be a retina of an eye 25 of a subject, but may alternatively be another part of the eye 25, such as an anterior region of the eye 25, for example. The axial displacements are caused by a relative motion of the OCT imaging system 30 and the imaging target 20, which varies a distance between the OCT imaging system 30 and the imaging target 20 during acquisition of the B-scans by the OCT imaging system 30. The axial displacement may be understood as a displacement along a propagation direction of an OCT light beam 40 that is incident on the eye 25 during use of the OCT imaging system 30 to image the retina.

The OCT imaging system 30 employs an ophthalmic scanner to scan the OCT imaging light beam 40 across the imaging target 20 to acquire the C-scan data, which is processed by the data processing apparatus 10. The data processing apparatus 10 may, as in the present example embodiment, be provided as a stand-alone processor such as a PC or laptop, which can be communicatively coupled to the OCT imaging system 30 (directly or via a network, such as the Internet) to receive C-scan data therefrom. Alternatively, the data processing apparatus 30 may be provided as part of the OCT imaging system 30. The OCT imaging system 30 may be any kind of OCT scanner well-known to those skilled in the art, which is capable of acquiring OCT data from the subject's eye 25.

As illustrated in FIG. 1, the data processing apparatus 10 of the present example embodiment comprises a correction data generator module 2, which is configured to generate the correction data by determining, for each pair of adjacent B-scans of a plurality of pairs of adjacent B-scans in the sequence, a respective indicator of an axial shift between respective representations of a common ocular feature in the adjacent B-scans. The axial shift may, as in the present example embodiment, represent a shift (or offset) between the common ocular feature in the adjacent B-scans along an axis of the B-scans that corresponds to the axial direction (i.e. the direction in which the data in each A-scan of the A-scans, which make up the B-scan, is arrayed, the data having been obtained through measurements at various depths along the propagation direction of the OCT light beam 40 which is incident on the eye 25). In the present example embodiment, the sequence of B-scans that is processed by the correction data generator module 2 comprises the complete sequence of B-scans forming the C-scan data that has been acquired by the OCT imaging system 30. However, it should be noted that the sequence of B-scans processed by the correction data generator module 2 need not be the aforementioned complete sequence, and may alternatively comprise a subset of the complete sequence, for example a subset containing every other B-scan in the complete sequence of B-scans.

The data processing apparatus 10 further comprises a reliability indicator generator module 4, which is arranged to generate the reliability indicator 5. More specifically, the reliability indicator generator module 4 is arranged to calculate, using pairs of B-scans in the sequence of B-scans, respective values of a metric which are indicative of respective speeds or respective accelerations of the imaging target relative to the OCT imaging system when the pairs of B-scans were acquired. The reliability indicator generator module 4 is further arranged to determine if at least a predetermined number of the calculated values of the metric exceed a threshold value. In a case where at least the predetermined number of calculated values of the metric are determined to exceed the threshold value, the reliability indicator generator module 4 is arranged to set the reliability indictor 5 to indicate that the correction data is unreliable. However, in a case where at least the predetermined number of calculated values of the metric are determined to not exceed the threshold value, the reliability indicator generator module 4 is arranged to set the reliability indictor 5 to indicate that the correction data is reliable.

The data processing apparatus 10 may, as in the present example embodiment illustrated in FIG. 1, further comprise a displacement compensation module 6, which is arranged to use the correction data to compensate for the axial displacements between the B-scans in the sequence of B-scans caused by the relative motion of the OCT imaging system 30 and the imaging target 20 during acquisition of the B-scans by the OCT imaging system 30. In some example embodiments, the displacement compensation module 6 is arranged to perform the aforementioned compensation only in the case where reliability indicator 5 has been set to indicate that the correction data is reliable.

A C-scan can be rendered to provide a three-dimensional image of a portion of the eye 25, and comprises a sequence of B-scans that are typically acquired by scanning the OCT light beam 40 in a raster pattern or the like across a two-dimensional region of the eye 25. Each B-scan is acquired by scanning the OCT light beam 40 in a single direction (for example, along an X-axis on the surface or the retina, for example) to record a two-dimensional, cross-sectional view (along the X and Z axes) of the region of the eye 25. Each B-scan comprises a plurality of A-scans, wherein each A-scan provides image data representing the axial/depth direction of the eye 25 (i.e. along the Z-axis) for a single lateral point in the eye 25.

Figure 2A:
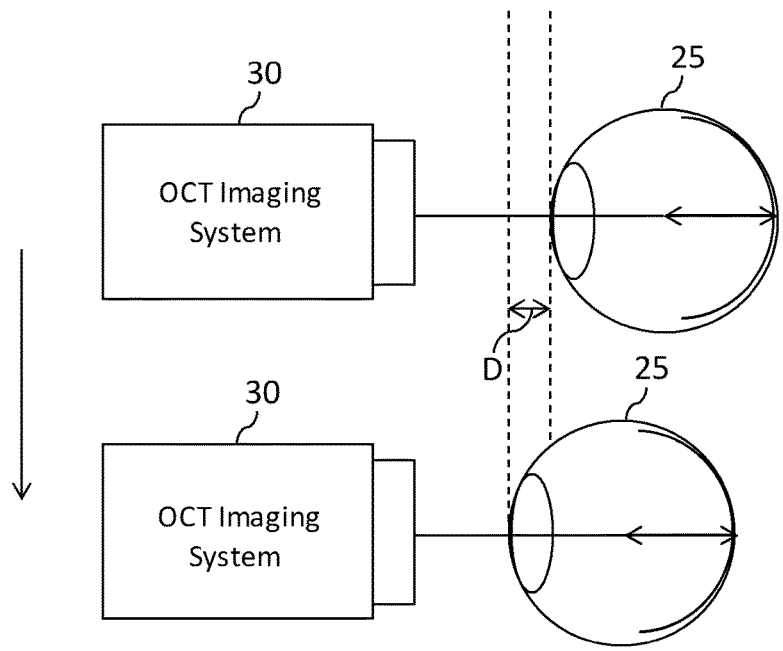
FIG. 2A illustrates an example of a movement of a subject which causes the distance between the subject's retina and an OCT imaging system to vary during imaging of the retina by the OCT imaging system.

FIG. 2A illustrates an example of a movement of the imaging target 20 (i.e. the retina, in the present example) relative to the OCT imaging system 30, which causes the distance between the retina and the OCT imaging system 30 to vary during the acquisition of C-scan data. As shown in the example of FIG. 2A, the motion of the subject during the acquisition of the B-scans causes the distance between the retina and the OCT imaging system 30 to be reduced by a distance D (along the axial direction).

Figure 2B:
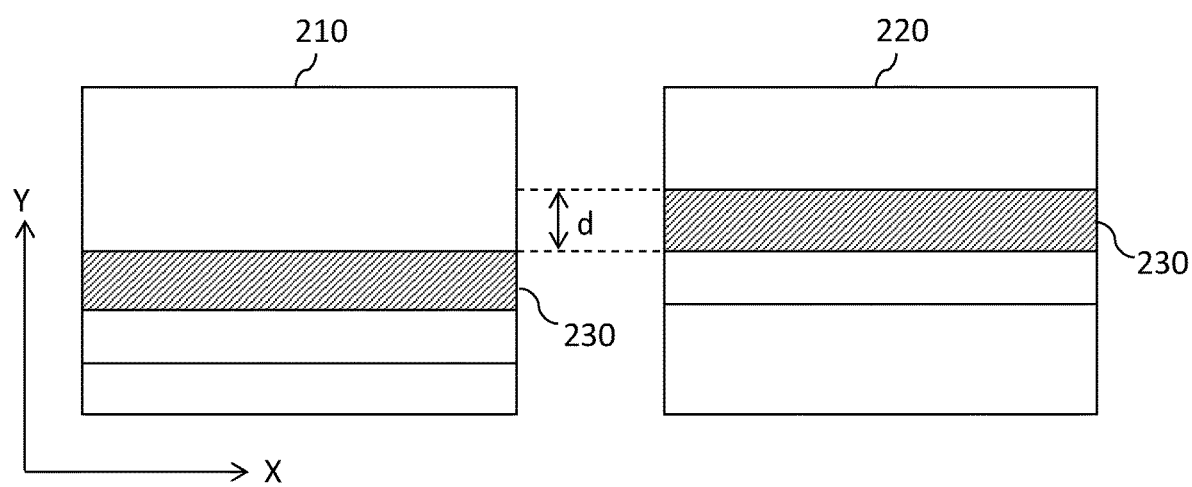
FIG. 2B illustrates an example of an axial shift between a common ocular feature in a pair of adjacent B-scans in a sequence of B-scans acquired by the OCT imaging system, the axial shift being caused by the movement of the retina illustrated in FIG. 2A.

FIG. 2B illustrates an axial shift in the location of a common ocular feature, which is observed in a pair of adjacent B-scans, labelled 210 and 220, that have been captured before and after the relative movement of the eye 25 and the OCT imaging system 30 shown in FIG. 2A. In the present example, the common ocular feature in the pair of adjacent B-scans is a retinal layer 230 of the eye 25. As shown in FIG. 2B, due to the movement of the retina that occurs during the acquisition of the B-scans, the location of retinal layer 230 in B-scan 220 is offset by a distance of d pixels along the Y-axis of the B-scans relative to its location in B-scan 210. In FIG. 2B, the Y-axis of B-scans 210 and 220 represents the axial direction, while the X-axis represents a lateral direction along the surface of the retina. If uncorrected, the axial shift of the retinal layer 230 in the adjacent B-scans would cause motion artefacts to appear in renderings of the C-scan data, which may hinder a proper diagnosis or measurement of the underlying feature in the retina being performed.

Figure 3:
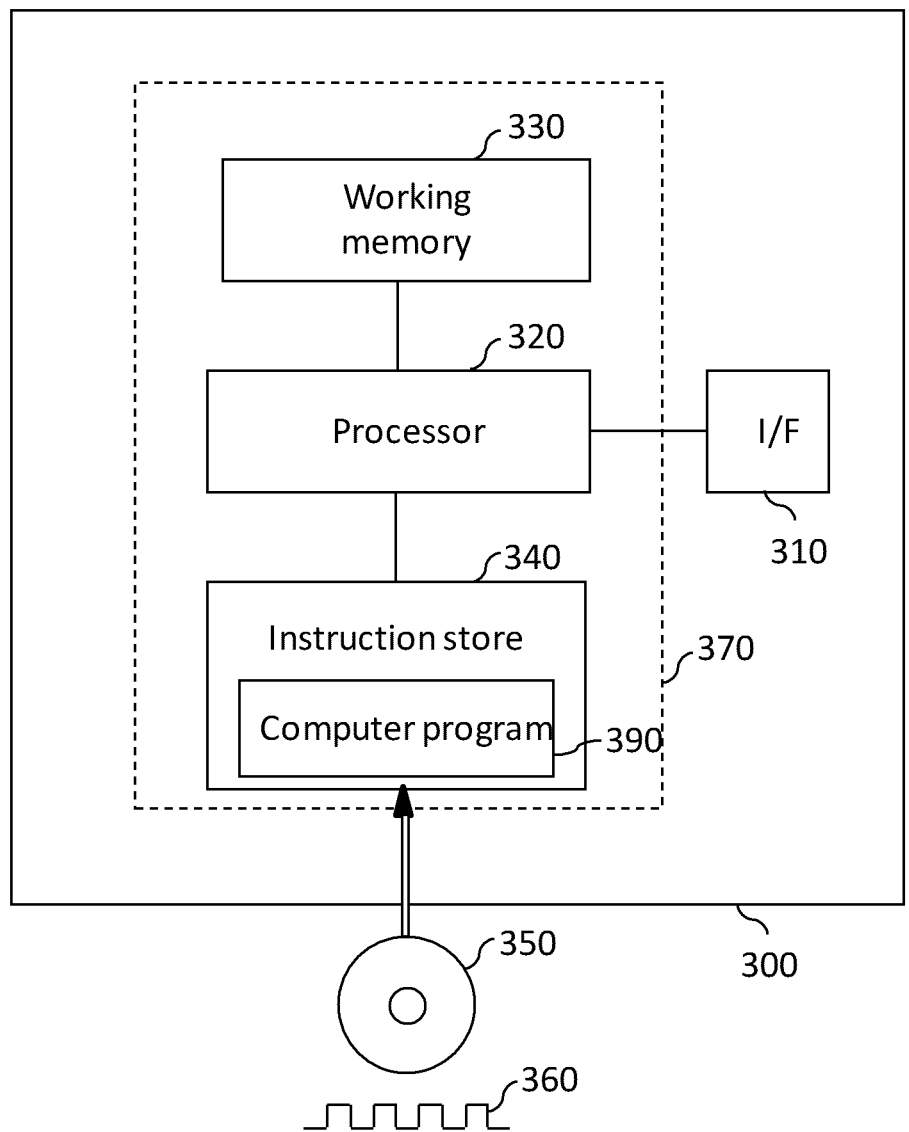
FIG. 3 is a block diagram illustrating an example implementation in programmable signal processing hardware of the data processing apparatus of the example embodiment herein.

FIG. 3 is a schematic illustration of a programmable signal processing hardware 300, which may be configured to process C-scan data using the techniques described herein and which can function as the correction data generator module 2, the reliability indicator generator module 4, and the displacement compensation module 6 of the first example embodiment.

The programmable signal processing apparatus 300 comprises a communication interface (I/F) 310, for communicating with the OCT imaging system 30 to receive C-scan data therefrom. The signal processing apparatus 300 further comprises a processor (e.g. a Central Processing Unit, CPU, and/or a Graphics Processing Unit, GPU) 320, a working memory 330 (e.g. a random access memory) and an instruction store 340 storing a computer program 390 comprising the computer-readable instructions which, when executed by the processor 320, cause the processor 320 to perform various functions including those of the correction data generator module 2, the reliability indicator generator module 4, and the displacement compensation module 6 described herein. The working memory 330 stores information used by the processor 320 during execution of the computer program 390. The instruction store 340 may comprise a ROM (e.g. in the form of an electrically-erasable programmable read-only memory (EEPROM) or flash memory) which is pre-loaded with the computer-readable instructions. Alternatively, the instruction store 340 may comprise a RAM or similar type of memory, and the computer-readable instructions of the computer program 390 can be input thereto from a computer program product, such as a non-transitory, computer-readable storage medium 350 in the form of a CD-ROM, DVD-ROM, etc. or a computer-readable signal 360 carrying the computer-readable instructions. In any case, the computer program 390, when executed by the processor 320, causes the processor 320 to execute a method of processing the C-scan data as described herein. It should be noted, however, that the correction data generator module 2, the reliability indicator generator module 4, and the displacement compensation module 6 may alternatively be implemented in non-programmable hardware, such as an application-specific integrated circuit (ASIC).

Figure 4:
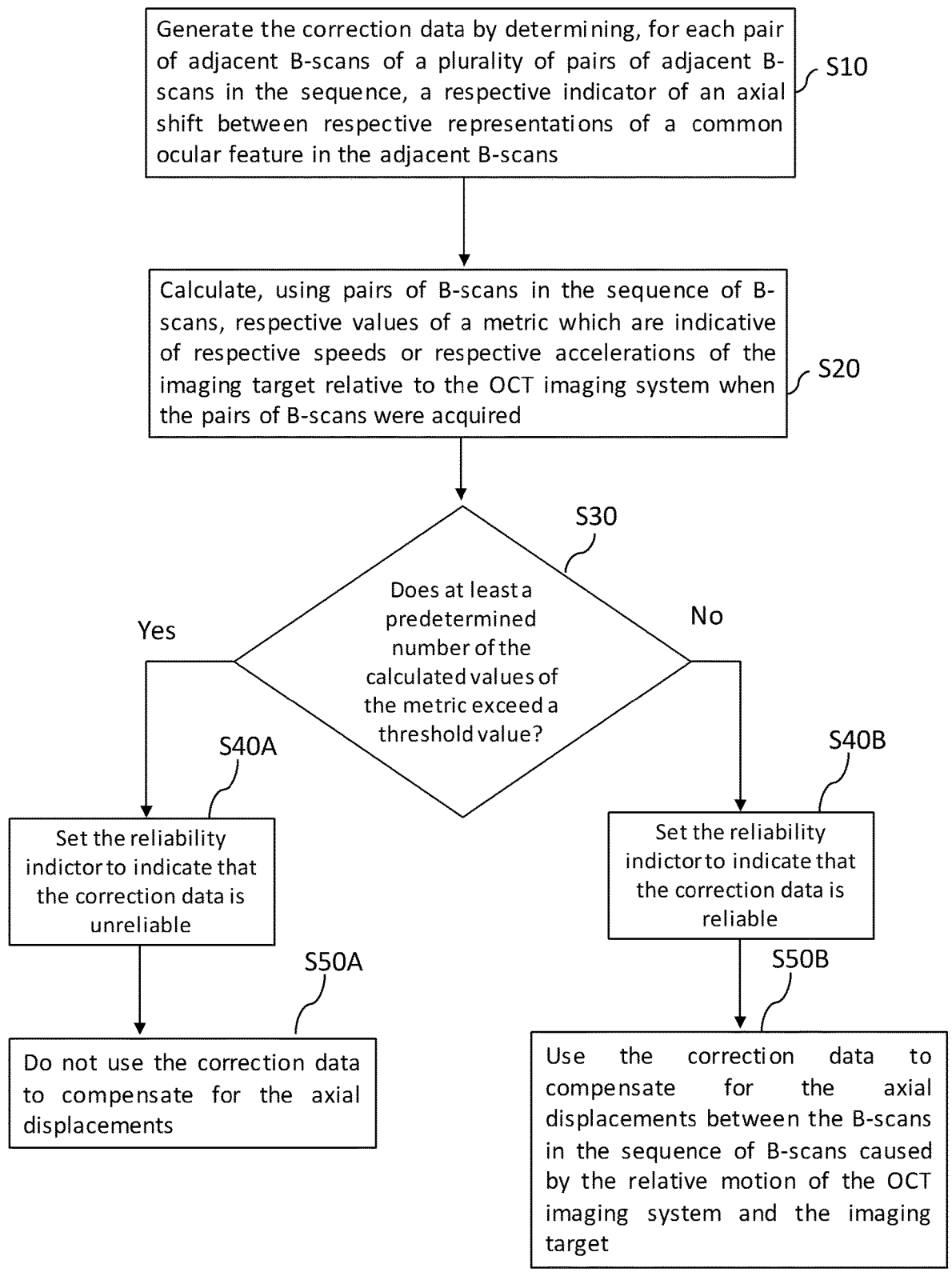
FIG. 4 is a flow diagram illustrating a method by which the data processing apparatus of FIG. 1 processes C-scan data comprising a sequence of B-scans to generate correction data for compensating axial displacements between B-scans in the sequence, and to further generate a reliability indicator which indicates a reliability of the correction data.

FIG. 4 is a flow diagram illustrating a method by which the data processing apparatus of FIG. 1 processes C-scan data comprising a sequence of B-scans to generate correction data for compensating axial displacements between B-scans in the sequence of B-scans, and a reliability indicator which indicates a reliability of the generated correction data.

In step S10 of FIG. 4, the correction data generator module 2 generates the correction data by determining, for each pair of adjacent B-scans of a plurality of pairs of adjacent B-scans in the sequence, a respective indicator of an axial shift between respective representations of a common ocular feature in the adjacent B-scans. The respective indicator of the axial shift may, as in the present example embodiment, be a distance between the respective coordinates of the common ocular feature in the pair of adjacent B-scans, along an axis of the B-scans that corresponds to the axial direction described above. However, the indicator of the axial shift is not limited in this regard, and may alternatively be a value that is determined based on the distance. As an example, for a sequence of N+1 B-scans, $B_k$, for k=1, 2, ..., N+1, it is possible to derive a set of N indicators $S_i$, for i=1, 2, ..., N, from the N corresponding pairs of B-scans in the sequence of B-scans, wherein indicator $S_i$ is derived from B-scans $B_{k=i}$ and $B_{k=i+1}$, and is indicative of the axial shift between respective representations of a common ocular feature in the pair of B-scans $B_{k=i}$ and $B_{k=i+1}$. The indicator index i thus corresponds to the location of the pair of adjacent B-scans in the sequence of B-scans that yielded the indicator $S_i$.

The indicator of the axial shift may, as in the present example embodiment, be determined for each pair of adjacent B-scans by calculating a cross-correlation between the pair of adjacent B-scans and determining, as the indicator, an offset between the B-scans corresponding to a peak in the calculated cross-correlation. The cross-correlation may, for example, be a normalized two-dimensional cross-correlation of the pair of adjacent B-scans that determines an offset (along both axes of the B-scan) in the location of a representation of an ocular feature in one B-scan (of the pair of B-scans) relative to the location of a representation of the same ocular feature in the other B-scan. However, only the determined offset along an axis of the B-scan that corresponds to the axial direction may be taken as the indicator of the axial shift between respective representations of the common ocular feature in the pair of adjacent B-scans. In some circumstances, where lateral motion of the eye during the acquisition of the B-scans is negligible, a one-dimensional cross-correlation of the pair of adjacent B-scans may be performed, and the offset between the B-scans corresponding to a peak in the calculated one-dimensional cross-correlation may be taken as the indicator of the axial shift.

Although the indicator of the axial shift is calculated using cross-correlation in the present example embodiment, any other suitable method may alternately be employed. For example, in an alternative embodiment, the indicator of the axial shift may be determined for each pair of the adjacent B-scans by identifying respective locations of the common ocular feature in the B-scans of the pair of adjacent B-scans, and determining a displacement between the identified locations along an axis of the B-scans that corresponds to the axial direction as described above. The respective locations of the common ocular feature in the pair of adjacent B-scans may be identified, for example, using a machine-learning algorithm or any other suitable image processing algorithm.

In step S20 of FIG. 4, the reliability indicator generator module 4 calculates, using pairs of B-scans in the sequence of B-scans, respective values of a metric which are indicative of a speed and/or an acceleration of the imaging target 20 relative to the OCT imaging system 30 when the pairs of B-scans were acquired. The metric may, as in the present example embodiment, be a speed metric that is indicative of a speed (in the axial direction) of the imaging target 20 relative to the OCT imaging system 30.

The speed metric may, as in the present example embodiment, be calculated using the indicators that have been determined in step S10 of FIG. 4 using adjacent pairs of B-scans in the sequence of B-scans. As each indicator is indicative of an axial shift of a common ocular feature in a pair adjacent B-scans, the indicator value, when divided by the time between the adjacent B-scans, is representative of the speed of the imaging target 20 relative to the OCT imaging system 30. However, it should be understood that the speed metric need not be calculated using on adjacent B-scans, and may instead be calculated based on an axial shift of a common ocular feature in a non-adjacent pair of B-scans in the sequence of B-scans. More generally, the determined axial shift of the common ocular feature in the pair of B-scans, divided by the time interval between the capture of the B-scans in the pair of B-scans, provides an indication of a rate of axial movement of the common ocular feature, and is therefore indicative of the speed of the relative motion of the imaging target 20 and the OCT imaging system 30. The metric may, as in the present example embodiment, be calculated for each adjacent pair of B-scans in the sequence, but may alternatively be calculated for only a subset of all acquired B-scan pairs, as previously mentioned.

In step S30 of FIG. 4, the reliability indicator generator module 4 determines if at least a predetermined number of calculated values of the metric exceed a threshold value. In the case that at least the predetermined number of calculated values of the metric is determined to exceed the threshold value, the reliability indicator generator module 4 sets, in step S40A of FIG. 4, the reliability indictor 5 to indicate that the correction data is unreliable. On the other hand, in the case that fewer than the predetermined number of calculated values of the metric are determined in step S30 to exceed the threshold value, the reliability indicator generator module 4 sets the reliability indictor 5, in step S40B of FIG. 4, to indicate that the correction data is reliable. In the present example embodiment, where the metric is a speed metric, the threshold value used in step S30 of FIG. 4 may correspond to a maximum physically possible speed of the imaging target 20 which can be expected to occur during capture of the OCT C-scan data. Any calculated values of the metric that exceed this threshold may be considered anomalies that are caused by spurious correlation between B-scans, rather than actual relative motion of the imaging target 20 and the OCT imaging system 30. The predetermined number in step S30 of FIG. 4 may thus be set based on a maximum number of anomalies that can be accepted before the correction data is considered unreliable.

Although the metric is a speed metric in the present example embodiment, the metric calculated in step S20 of FIG. 4 may take other forms, for example an acceleration metric, which is indicative of an acceleration of the imaging target 20 relative to the OCT imaging system 30. When the metric is taken to be an acceleration metric in step S20 of FIG. 4, the threshold value in step S30 may be set based on a maximum value of the acceleration of the imaging target 20 that is considered realistic or physically possible. The reliability indicator generator module 4 may evaluate the acceleration metric by determining a first value indicative of a rate of axial shift of a common ocular feature in a first pair of B-scans, and a second value indicative of a rate of axial shift of a common ocular feature in a second pair of B-scans, wherein the first pair differs from the second pair by at least one B-scan. The reliability indicator generator module 4 may further evaluate the acceleration metric based on a difference between the first value and the second value. For example, for a first pair of B-scans captured at times T1 and T2, and having a determined rate of axial shift value of A1, and a second pair of B-scans captured at times T3 and T4 (occurring after T1 and T2) and having a determined rate of axial shift of A2, the acceleration metric may be calculated as:

$$\frac{A2 - A1}{0.5(T4 + T3) - 0.5(T2 + T1)}$$

However, it should be understood that the acceleration metric is not limited to the above form and may be calculated based on a difference between A2 and A2, and another measure of the temporal separation of the two pairs of B-scans, for example T3−T1 or T4−T2.

In some example embodiments, in the case where the reliability indicator 5 has been set to indicate that the correction data is reliable, the displacement compensation module 6 may use the correction data to compensate for the axial displacements between the B-scans in the sequence of B-scans caused by the relative motion of the OCT imaging system 30 and the imaging target 20, as shown in step S50B of FIG. 4. On the other hand, in the case where the reliability indicator 5 has been set to indicate that the correction data is unreliable, the displacement compensation module 6 does not perform the aforementioned compensation for axial displacements between the B-scans using the correction data, as shown in step S50A. For example, when the reliability indicator has been set to indicate the correction data to be unreliable, the sequence of B-scans may be discarded and/or indicated to the user to be unreliable, and new C-scan data comprising a new sequence of B-scans may be captured by performing a new OCT scan of the imaging target 20. The new sequence of B-scans may be processed using the process in FIG. 4 to generate new correction data and a new reliability indicator.

The variation of determined indicators with the locations of the corresponding pairs of adjacent B-scans in the sequence may comprise high-frequency components that are caused by noisy data and/or data tainted by image artefacts caused by blinking and the line, and a consequently spurious correlation between adjacent B-scans. As such, the indicators which are directly generated based on adjacent B-scans may be unsuitable for use in compensating the axial displacements of the B-scans, without some form of pre-filtering to remove outliers or anomalies. Accordingly, in some example embodiments, a frequency component of the variation that is indicative of a relative motion of the OCT imaging system 30 and the imaging target 20 during the acquisition of the B-scans, may be determined and used to perform the compensation in step S50B.

Figure 5:
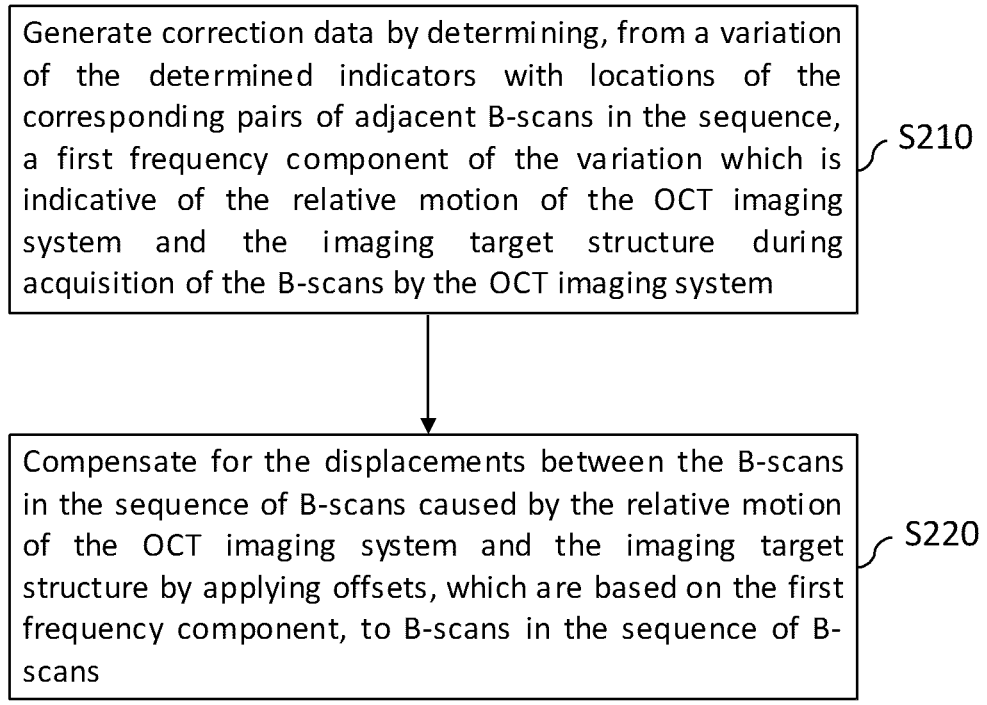
FIG. 5 illustrates a method which may be performed by the data processing apparatus to determine a first frequency component of the variation which is indicative of the relative motion of the OCT imaging system and the retina during the acquisition of the B-scans, in accordance with a first example implementation described herein.

FIG. 5 is a flow diagram illustrating a method which may be performed by the correction data generator module 2 to determine a first frequency component of the variation which is indicative of the relative motion of the OCT imaging system 30 and the imaging target 20 during the acquisition of the B-scans, in accordance with a first example implementation described herein.

As shown in step S210 of FIG. 5, the correction data generator module 2 may generate the correction data by determining, from a variation of the determined indicators with locations of the corresponding pairs of adjacent B-scans in the sequence, a first frequency component of the variation which is indicative of the relative motion of the OCT imaging system 30 and the imaging target 20 during acquisition of the B-scans by the OCT imaging system 30. In step S220 of FIG. 5, the displacement compensation module 6 may compensate for the displacements between the B-scans in the sequence of B-scans caused by the relative motion of the OCT imaging system 30 and the imaging target 20 by applying offsets, which are based on the first frequency component, to B-scans in the sequence of B-scans.

For example, in step S210 of FIG. 5, the correction data generation module 2 may generate the first frequency component of the variation by fitting an $n^{th}$ order polynomial to the variation of indicators. Then, in step S220 of FIG. 5, the displacement compensation module 6 may compensate the axial displacements between adjacent B-scans in the sequence based on the $n^{th}$ order polynomial, for example, by using one or more values of the $n^{th}$ order polynomial to offset one or more B-scans in the sequence of B-scans. It should be noted, that, in some example embodiments, the compensation performed in step S220 of FIG. 5 may be conditional on the reliability indicator having been set to indicate that the correction data is reliable, in step S40A of FIG. 4.

It should also be noted that the first frequency component need not be determined by polynomial fitting at step S210 of FIG. 5, and other suitable methods may be used. For example, in an alternative embodiment, the correction data generator module 2 may instead generate the first frequency component at step S210 by low-pass filtering the variation of determined indicators to remove high-frequency components of the variation that do not originate from the relative movement of the imaging target 20 and the OCT imaging system 30.

Figure 6:
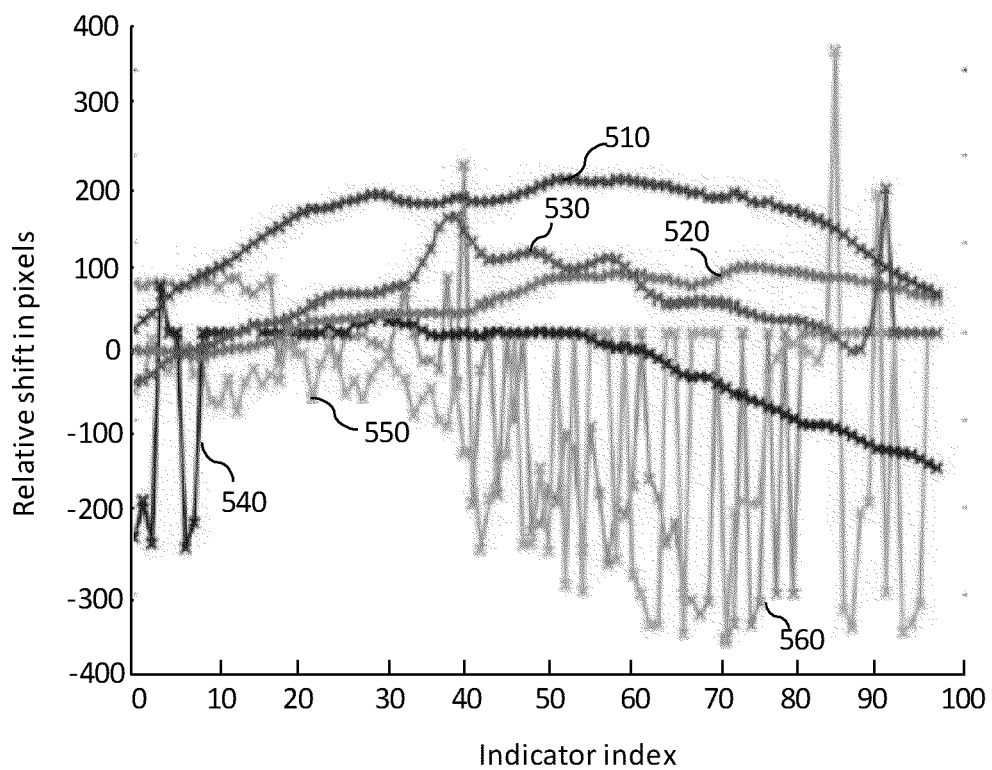
FIG. 6 illustrates plots of several sequences of indicator values, each indicator value indicating an axial shift between a common retinal feature in a pair of B-scans in the sequence of B-scans. The plots illustrate how the indicator values vary with the locations of the corresponding pairs of adjacent B-scans in the sequence.

FIG. 6 illustrates six example plots that correspond to six different sets of indicators determined from six different sequences of B-scans of the imaging target 20 in eye 25.

Each plot illustrates the variation of determined indicators for a corresponding sequence of B-scans, wherein each indicator is calculated by cross-correlating a pair of adjacent B-scans in the sequence and is representative of an axial shift between the pair of adjacent B-scans. In the example of FIG. 6, the indicator determined for each pair of adjacent B-scans is plotted against indicator index i, that also corresponds to a pair of adjacent B-scans and is therefore representative the location of the pair of adjacent B-scans in the sequence of B-scans.

As shown in FIG. 6, the variation of the determined indicators with the locations of the corresponding pairs of adjacent B-scans in the sequence of B-scans may comprise multiple frequency components attributed to different causes. For example, in addition to a frequency component that arises due to a relative motion of the eye 25 and the OCT imaging system 30 during the acquisition of the sequence of B-scans, the variation may also comprise various other frequency components such as, for example, a low-frequency component caused by a curvature of the retina, which can be observed in plots 510, 520 and 530. In particular, the frequency component resulting from the curvature of the retina may be lower than the frequency component caused by a motion of the eye 25, since the rate of axial shift of an ocular feature in a sequence of B-scans due to the curvature of the retina will likely be lower than the axial shift resulting from motion of the subject. Furthermore, the variation of indicators with the locations of the corresponding pairs of adjacent B-scans in the sequence, may also comprise high-frequency components resulting from spurious correlation between adjacent B-scans. Such high-frequency components can be observed in plots 540, 550 and 560, each of which displays a large number of peaks that contribute to the presence of high-frequency components in these variations of indictor values.

In some example embodiments, the imaging target 20 may have a curvature. In these embodiments, directly compensating the B-scans using the indicators (determined by cross-correlating adjacent B-scans or by performing feature identification using the adjacent B-scans) may cause the imaging target 20 to be rendered without its curvature. Accordingly, in some embodiments, for more accurate diagnosis and/or measurement of an ocular feature, it may be desirable for the curvature of the imaging target 20 to be retained in the rendered C-scan (that is formed by the compensated B-scans).

Figure 7:
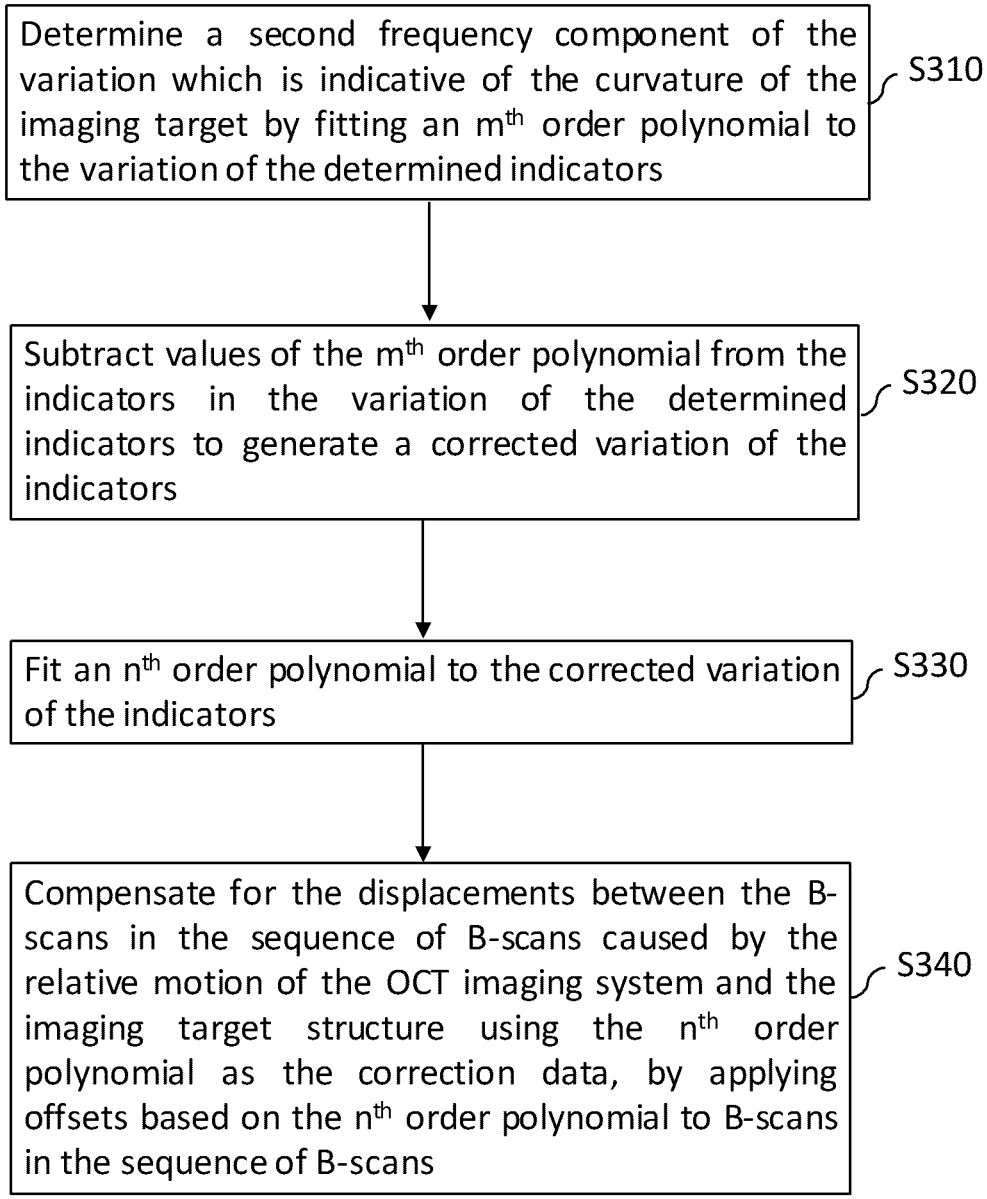
FIG. 7 illustrates a method which may be performed by the data processing apparatus to determine the first frequency component of the variation, in accordance with a second example implementation described herein.

FIG. 7 illustrates a method which may be performed by the correction data generator module 2 to determine the first frequency component in step S210 of FIG. 5, in embodiments where the imaging target 20 has a curvature. In step S310 of FIG. 7, the correction data generator module 2 determines a second frequency component of the variation, which is indicative of the curvature of the imaging target 20 (which is the retina in the present example). The correction data generator module 2 may, as in the present example embodiment, determine the second frequency component by fitting an $m^{th}$ order polynomial to the variation of the determined indicators, where m is an integer. For example, the sequence of determined indicators $S_i$, i=1, 2, ..., N, may be represented as a set of N data points ($x_i$, $S_i$), i=1, 2, ..., N. An $m^{th}$ order polynomial $P^m(x)$ may then be fitted to the sequence of indicators $S_i$, i=1, 2, ..., N, by fitting the $m^{th}$ order polynomial to the set of equivalent datapoints ($x_i$, $S_i$), i=1 to N, that represent the sequence of indicators, where $x_i$ is X-coordinate value associate with indicator $S_i$ in the data point ($x_i$, $S_i$).

In step S320 of FIG. 7, the correction data generator module 2 subtracts values of the $m^{th}$ order polynomial from the indicators in the variation of the determined indicators to generate a corrected variation of the indicators. For example, for the sequence of determined indicators $S_i$, i=1, 2, ..., N, represented in data point form ($x_i$, $S_i$), i=1, 2, ..., N, and for an $m^{th}$ order polynomial $P^m(x)$ fitted to the sequence of indicators, the corrected variation of the indicators may be given by the set of values, $C_i = S_i - P^m(x_i)$, i=1, 2, ..., N.

In the present example, the second frequency component of the variation that is indicative of the curvature of the retina is determined by fitting a $2^{nd}$ order polynomial to the variation of the determined indicators. However, depending on the expected curvature of the imaging target 20, a different order polynomial may be used. The $2^{nd}$ order polynomial may, as in the present example embodiment, be fitted using the least squares method to minimize a sum of squared residuals between the variation of the indicators and the $2^{nd}$ order polynomial, although any suitable polynomial regression method may otherwise be used.

In step S330 of FIG. 7, the correction data generator module 2 determines the first frequency component of the variation of indicators by fitting an $n^{th}$ order polynomial to the corrected variation of the indicators $C_i$, i=1, 2, ..., N, where n is an integer larger than m. The first frequency component, which is indicative of the relative motion of the OCT imaging system 30 and the imaging target 20, is thus represented by the $n^{th}$ order polynomial. As an example, the corrected variation of indicators $C_i$, i=1, 2, ..., N, may be represented as data points ($x_i$, $C_i$), i=1, 2, ..., N and the $n^{th}$ order polynomial $P^n(x)$ may be fitted to the data points ($x_i$, $C_i$), i=1, 2, ..., N. In some embodiments, the correction data generator module 2 may first apply a smoothing operation (for example, by using a moving average filter) to the corrected variation of the indicators before fitting the $n^{th}$ order polynomial, in order to avoid overfitting to data points that result from spurious correlation. In the present example embodiment, a $5^{th}$ order polynomial is fitted to the corrected variation of the indicators as the $n^{th}$ order polynomial. However, the value of n is not limited in this regard, and may be selected in any suitable way. In some embodiments, the value of n may be selected based on scan parameters used by the OCT imaging system 30 to obtain the C-scan data, such as, the scan density (e.g. the number of B-scans captured per unit area of the retina) and the scan duration (i.e. the total time taken to acquire the C-scan data). As a general rule, a higher value of n may be selected for the $n^{th}$ order polynomial for a higher scan density and for longer scan durations.

Although the curvature of the retina is determined in the present example embodiment by fitting a low-order polynomial function to the variation of indicators, other methods may also be used instead. For example, the correction data generator module 2 may alternatively determine the second frequency component, which is indicative of the curvature of the retina, by performing a discrete Fourier transform on the variation of indicators ($x_i$, $S_i$), i=1, 2, ..., N, to determine frequency domain samples for the variation of indicators. The correction data generator module 2 may further extract a subset of the frequency domain samples that corresponds to a predetermined frequency range associated with the curvature of the retina. The frequency range may be determined empirically based on an expected curvature of the retina, for example. The frequency determination module 4 may further perform an inverse Fourier transform on the subset of frequency domain samples to obtain values corresponding to the second frequency component, which may be subtracted from the indicators in the variation of the determined indicators to generate the corrected variation of the indicators.

In some example embodiments, instead of performing an inverse Fourier transform on the subset of frequency domain samples and subtracting the obtained values corresponding to the second frequency component from the variation of indicators, the correction data generator module 2 may instead process the frequency domain samples by setting to zero the subset of frequency domain samples and perform inverse Fourier transform on the processed frequency domain samples in order to directly obtain the corrected variation of the indicators. Alternatively, the correction data generator module 2 may bandpass filter the variation of the indicators to remove the second frequency component corresponding to the curvature of the retina, in order to determine a corrected variation of indicators, and then fit the $n^{th}$ order polynomial to the corrected variation of the indicators. The lower cut-off frequency of the bandpass filtering process may be selected based on the expected curvature of the retina.

It should be noted, however, that in cases where the spatial extent of the scan is small relative to the curvature of the retina, the curvature of the retina can be assumed to be negligible and therefore, the second frequency component need not be determined. In this case, the $n^{th}$ order polynomial may be fitted directly to the sequence of determined indicators $S_i$, i=1, 2, ..., N, and determined as the first frequency component that is indicative of the relative motion of the OCT imaging system 30 and the imaging target 20.

Upon determining the $n^{th}$ order polynomial in step S330 of FIG. 7, the displacement compensation module 6 may, in step S340 of FIG. 7, compensate for the displacements between the B-scans in the sequence of B-scans caused by the relative motion of the OCT imaging system 30 and the imaging target 20 during acquisition of the B-scans by the OCT imaging system 30 using the $n^{th}$ order polynomial as the correction data, by applying offsets based on the $n^{th}$ order polynomial to B-scans in the sequence of B-scans.

In the present example embodiment, the first frequency component is given by the nth order polynomial $P^n(x)$, and therefore, the displacement compensation module 6 may apply the offset by offsetting each B-scan in the sequence of B-scans based on a value of the $n^{th}$ order polynomial. For instance, for an $n^{th}$ order polynomial $P^n(x)$ that was fitted to the sequence of corrected variation of the indicators $C_i$, i=1, N (or, more specifically, fitted to the corresponding set of data points ($x_i$, $C_i$), i=1, 2, ..., N) in step S330 of FIG. 7, the set of values of $P^n(x_i)$, for i=1, 2, ..., N, of the $n^{th}$ polynomial can be determined. A mapping between the set of values of $P^n(x_i)$, for i=1, 2, ..., N and the B-scans in the sequence may be used, such that each value of the set of values $P^n(x_i)$, i=1, 2, ..., N, is used to offset a B-scan in the sequence of B-scans. In the present example, as the indicator $S_i$ is derived from B-scans $B_{k=i}$ and $B_{k=i+1}$, then the polynomial value $P^n(x_i)$ may be used to offset the B-scan $B_{k=i+1}$. However, as each indicator is indicative of an axial shift between adjacent B-scans in the sequence, the offset applied to each B-scan $B_k$ in the sequence of B-scans must also include the cumulative sum of the offset applied to each preceding B-scan in the sequence (namely, B-scans in the sequence with an index lower than k). In other words, for each B-scan $B_k$ in the sequence, an offset of $\Sigma_{i=1}^{k-1}P^n(x_i)$ may applied to the B-scan in order to correct for axial displacement.

As an example, for a C-scan comprising of a sequence of 100 B-scans that are denoted by $B_k$, k=1 to 100, an $n^{th}$ order polynomial, $P^n(x)$, may be determined from the variation of the indicators $S_i$, i=1, 2, . . . , 99 that is calculated from the 100 B-scans, by firstly subtracting the $m^{th}$ order polynomial, which is representative of the retinal curvature, from the variation of indicators, to obtain a corrected variation $C_i$, i=1, 2, . . . , 99 of indicators and then fitting the $n^{th}$ order polynomial to the corrected variation of indicators. The displacement compensation module 6 may further determine, from the corrected variation of indicators, the set of values $P^n(x_i)$, i=1, 2, . . . , 99 of the $n^{th}$ order polynomial $P^n(x)$. The set of values $P^n(x_i)$, for i=1, 2, . . . , 99 may subsequently be used to offset B-scans, $B_k$, k=1 to 100, respectively. For example, the displacement compensation module 6 may compensate for the displacement between the 100 B-scans by offsetting B-scan $B_2$ by the value of $P^n(x_1)$, offsetting B-scan $B_3$ by the value of $P^n(x_1)+P^n(x_2)$, and more generally, offsetting B-scan $B_k$ by an offset of $P^n(x_1)$.

It should be noted that, although the offsetting of the B-scans in step S340 of FIG. 7 is based on the values of the $n^{th}$ order polynomial, which was fitted to the sequence of corrected variation of the indicators $C_i$, i=1, . . . , N, in some other example embodiments, the sequence of corrected variation of the indicators $C_i$, i=1, N may be taken as the first frequency component and used to directly offset B-scans in the sequence of B-scans. For example, for each B-scan $B_k$ in the sequence, an offset of $\Sigma_{i=1}^{k-1}C_i$ may applied to the B-scan in order to correct for axial displacements of the eye 25.

In some example embodiments, the $n^{th}$ order polynomial fitted to the corrected variation of the indicators $C_i$, i=1, N is not used directly as the first frequency component to offset the B-scans in step S340 of FIG. 7. Instead, the correction data generator module 2 may determine the first frequency component in step S210 of FIG. 5 in accordance with a second example implementation, by further performing at least two iterations of a process comprising steps of:
  (i) calculating a plurality of residual values, each residual value calculated as a difference between an indicator in a variation of indicators and a corresponding value of an $n^{th}$ order polynomial;
  (ii) determining whether the plurality of residual values comprise an outlier value which exceeds a first positive threshold value or falls below a first negative threshold value;
  (iii) in case the plurality of residual values is determined to comprise the outlier value, removing the indicator corresponding to the outlier value from the variation of indicators to generate an updated variation of indicators and, in case the plurality of residual values are determined not to comprise the outlier value, ending the process and determining the $n^{th}$ order polynomial as the first frequency component; and
  (iv) fitting the $n^{th}$ order polynomial to the updated variation of indicators.

Each residual value in the plurality of residual values is calculated in the first iteration of the above process as a difference between an indicator in the corrected variation of the indicators and a corresponding value of the $n^{th}$ order polynomial fitted to the corrected variation of the indicators. Furthermore, each residual value in the plurality of residual values is calculated in each iteration of remaining one or more iterations of the above process as a difference between an indicator in the updated variation of indicators generated in a previous iteration of the process and a corresponding value of the $n^{th}$ order polynomial fitted to the updated variation of indicators generated in the previous iteration of the process.

Figure 8:
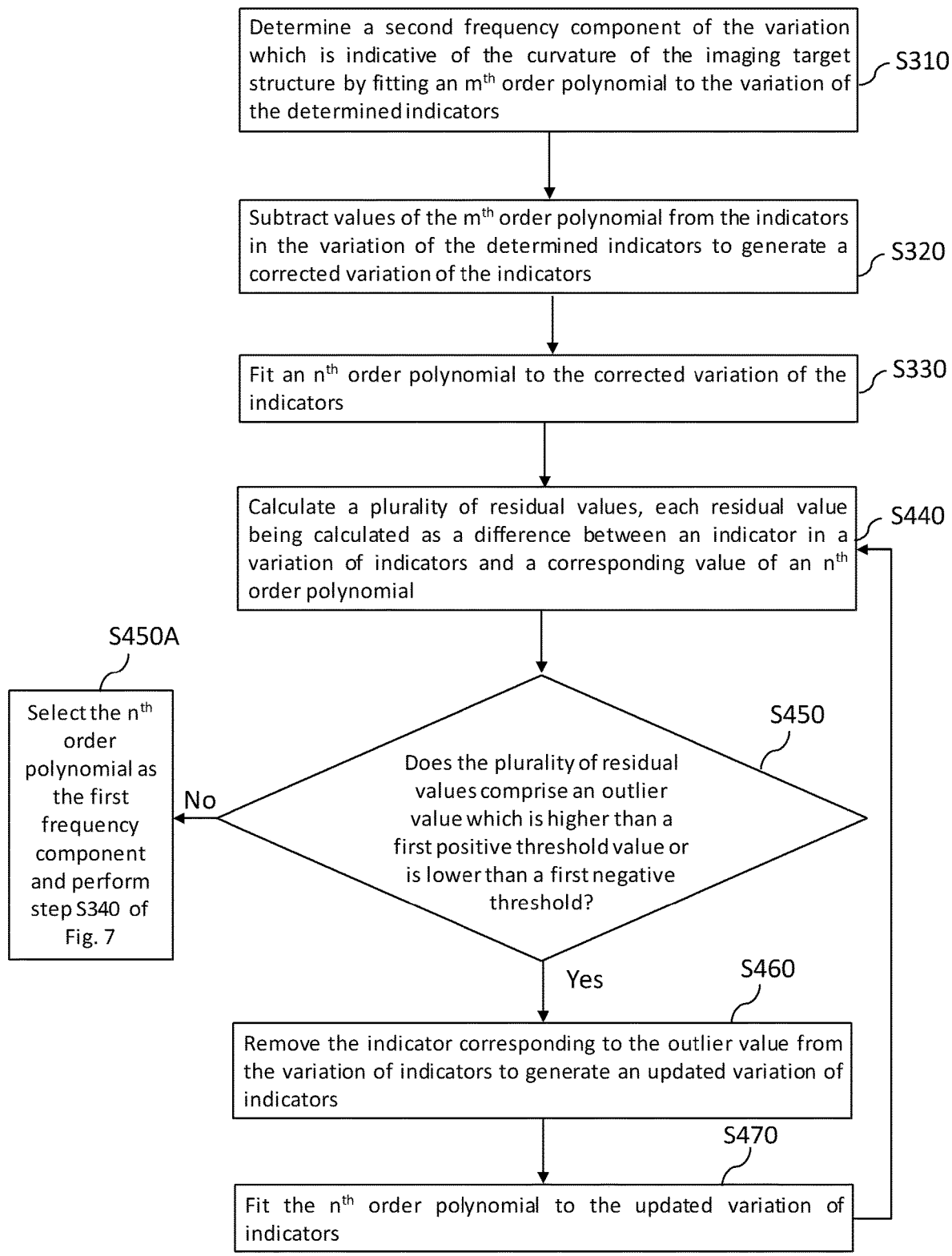
FIG. 8 illustrates a method which may be performed by the data processing apparatus to determine the first frequency component, in accordance with a third example implementation described herein.

FIG. 8 is a flow diagram illustrating a process which may be performed by the correction data generator module 2 to determine the first frequency component in accordance with a second example implementation. As shown in FIG. 8, the correction data generator module 2 may first perform steps S310, S320 and S330 of the process described above with reference to FIG. 7. In the second example implementation, however, after the $n^{th}$ order polynomial is determined in step S330, the $n^{th}$ order polynomial is not used directly to offset the B-scans in step S340. Instead, the correction data generator module 2 further calculates, in step S440 of FIG. 8, a plurality of residual values, each residual value being calculated as a difference between an indicator in a variation of indicators and a corresponding value of an $n^{th}$ order polynomial. In the present example, where the corrected variation of indicators $C_i$, i=1, 2, . . . , N is represented as data points $(x_i, C_i)$, i=1, 2, . . . , N, and the $n^{th}$ order polynomial is denoted $P^n(x)$, the plurality of residual values may be determined in step S440 of FIG. 7 as $R(x_i)=C_i-P^n(x_i)$, for I=1, 2, . . . , N.

In step S450 of FIG. 8, the correction data generator module 2 determines whether the plurality of residual values comprise an outlier value which is higher than a first positive predetermined threshold value or lower than a first negative predetermined threshold value. In response to determining that the plurality of residual values comprise an outlier value, the correction data generator module 2 removes, in step S460 of FIG. 8, the corrected indicator $C_i$ corresponding to the outlier value from the corrected variation of indicators $C_i$, i=1, 2, . . . , N to generate an updated variation of indicators $U_i$, for x=1 to N. Removing the corrected indicator $C_i$ corresponding to the outlier value may, for example, comprise setting the value of the corrected indicator $C_i$ to zero. For example, if it is determined that the residual value corresponding to corrected indicator $C_{i=p}$ is an outlier value, then the data point $(x_p, C_p)$ may be set to zero in the set of data points $(x_i, C_i)$, i=1, 2, . . . , N representing the corrected variation of indicators. It should be noted, however, that in some embodiments, instead of setting the corrected indicator $C_p$ corresponding to the outlier value to zero, the correction data generator module 2 may alternatively replace the corrected indicator $C_i$ corresponding to the outlier value with a new value, that may be based on one or more other values of $C_i$ that have residual values which are not determined as outliers at step S460, and obtained from these values by interpolation, for example.

In step S470 of FIG. 8, the correction data generator module 2 fits an $n^{th}$ order polynomial to the updated variation of indicators $U_i$, for x=1, 2, . . . , N. Then, the process of step S440 is repeated, this time to calculate a plurality of residual values, wherein each residual value is calculated as a difference between an indicator in the updated variation of indicators (determined in step S460) and a corresponding value of the $n^{th}$ order polynomial which has been fitted to the updated variation of indicators in step S470. After step S470 has been performed, steps S440, S450, S460 and S470 in FIG. 8 may be repeated until it is determined in step S450 that the plurality of residual values determined for an iteration does not contain an outlier value (or in an alternative implementation, contain a number of outlier values that is fewer than a predetermined number). In case that no outlier value is determined to be present in the plurality of residual values in step S450, then the process proceeds to step S450A, where the $n^{th}$ order polynomial that was used to generate the plurality of residual values is taken as the first frequency component, which is then used in step S340 of FIG. 7 to offset the B-scans in order to compensate for the displacements between the B-scans in the sequence of B-scans caused by the relative motion (in the axial direction) of the retina and the OCT imaging system 30. In particular, the correction data generator module 2 may offset the B-scans based on the values of the $n^{th}$ order polynomial in the same manner as previously described for step S340 of FIG. 7.

Figure 9:
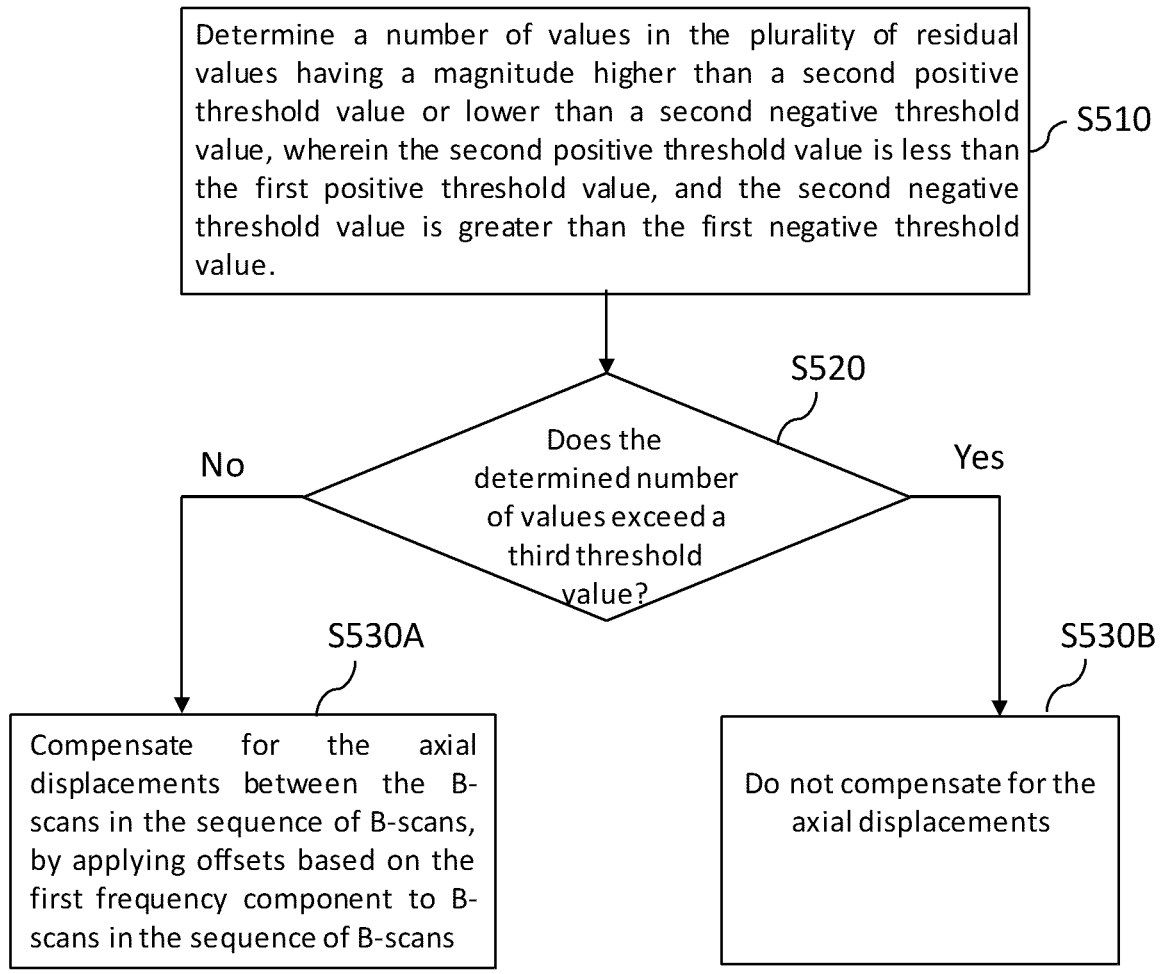
FIG. 9 illustrates a method which can be performed by the data processing apparatus to determine whether to compensate for the axial displacements between the B-scans in the sequence of B-scans, in accordance with an example embodiment herein.

In some example embodiments, when it is determined in step S450 of FIG. 8 that the plurality of residual values for an iteration does not contain any outlier, the correction data generator module 2 may further evaluate the plurality of residual values in order to determine whether the $n^{th}$ order polynomial that was used to obtain the plurality of residual values may be taken as the first frequency component and used to offset the B-scans in step S340 of FIG. 7. More specifically, referring to FIG. 9, the correction data generator module 2 may further determine, in step S510 of FIG. 9, a number of residual values among the plurality of residual values having a magnitude greater than a second positive threshold value or smaller than a second negative threshold value, wherein the second positive threshold value is smaller than the first positive threshold value in step S450 of FIG. 8; and the second negative threshold value is greater than the first negative threshold value in step S450 of FIG. 8. In step S520 of FIG. 9, the correction data generator module 2 determines if the number of residual values determined in step S510 of FIG. 9 exceeds a third threshold value. In response to determining that the number of residual values determined in step S510 of FIG. 9 does not exceed the third threshold value, correction data generator module 2 selects, in step S530A of FIG. 9, and as the first frequency component, the $n^{th}$ order polynomial that was used to generate the plurality of residual values (which does not contain any outliers), and performs step S340 of FIG. 7 by using the $n^{th}$ order polynomial as the first frequency component. On the other hand, if the correction data generator module 2 determines that the number of residual values determined in step S510 of FIG. 9 does exceed the third threshold value, then step S340 of FIG. 7 is not performed. This is because, when a significant number of the residual values is relatively high, this can be taken to indicative a poor fit of the $n^{th}$ order polynomial to the corrected variation of indicators (or the updated variation of indicators). As such, instead of correcting the axial displacement in the sequence of B-scans using the $n^{th}$ order polynomial, the sequence of B-scans may be discarded, and new C-scan data comprising a new sequence of B-scans may be captured by performing a new OCT scan of the imaging target 20. The new sequence of B-scans may be processed using any of the foregoing methods to generate correction data for compensating for axial displacements between B-scans in the sequence of B-scans caused by a relative motion of the OCT imaging system 30 and the imaging target 20.

Example Embodiment 2

In the first example embodiment and the variants thereof described above, the correction data may be derived from pairs of adjacent B-scans in the sequence of B-scans. However, in the data processing apparatus of the present example embodiment, the correction data used to compensate axial displacements between the B-scans is generated using trace scan data that serves as reference data against which acquired B-scans can be compared in order to determine the correction data. That is, instead of generating the correction data by determining, for each pair of adjacent B-scans of a plurality of B-scans in the sequence, a respective indicator of relative axial shift between respective representations of a common ocular feature in the adjacent B-scans, the correction data may be alternatively determined, for each B-scan of at least some of the B-scans in the sequence, a respective indicator of an axial shift between respective representations of a common ocular feature in the B-scan and the trace scan data.

Figure 10:
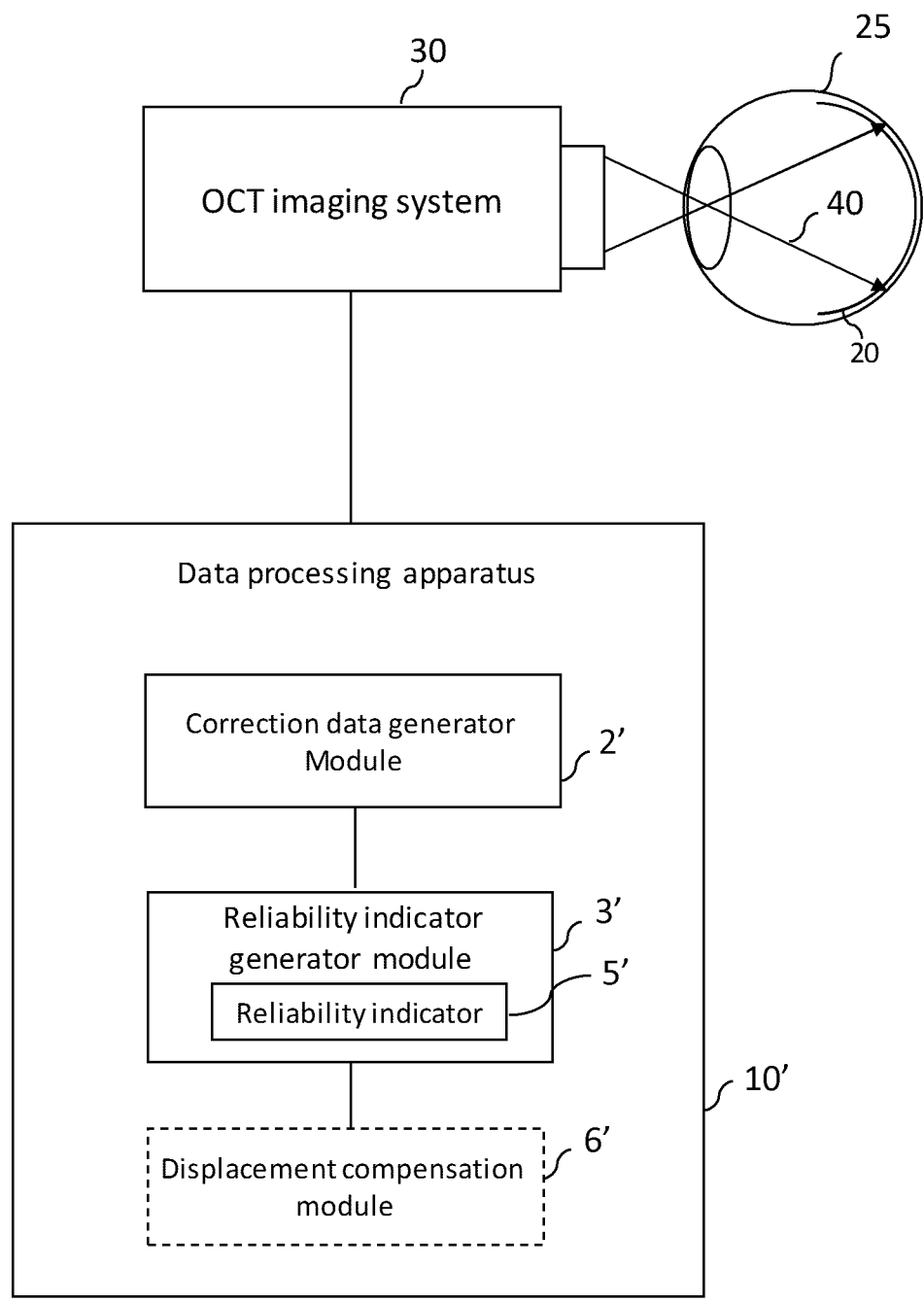
FIG. 10 is a schematic illustration of a data processing apparatus for processing C-scan data according to a second example embodiment herein.

FIG. 10 is a schematic illustration of a data processing apparatus 10' for processing C-scan data according to a second example embodiment herein. The data processing apparatus 10' is arranged to process C-scan data comprising a sequence of B-scans of an imaging target 20, which has been acquired by the OCT imaging system 30 scanning along corresponding scan lines that extend across the imaging target 20, together with trace scan data, to generate correction data for compensating for axial displacements between B-scans in the sequence of B-scans, and to generate a reliability indicator 5' which indicates a reliability of the generated correction data.

The trace scan data is acquired by the OCT imaging system 30 by performing a scan along a trace scan line, which crosses the scan lines. As in the first example embodiment, the axial displacements are caused by a relative motion of the OCT imaging system 30 and the imaging target 20 that varies a distance therebetween during acquisition of the B-scans by the OCT imaging system 30. As shown in FIG. 10, the data processing apparatus 10' comprises a correction data generator module 2', and a reliability data generator module 4'. Furthermore, the data processing apparatus 10' may, as in the present example embodiment, comprise a displacement compensation module 6'.

Figure 11:
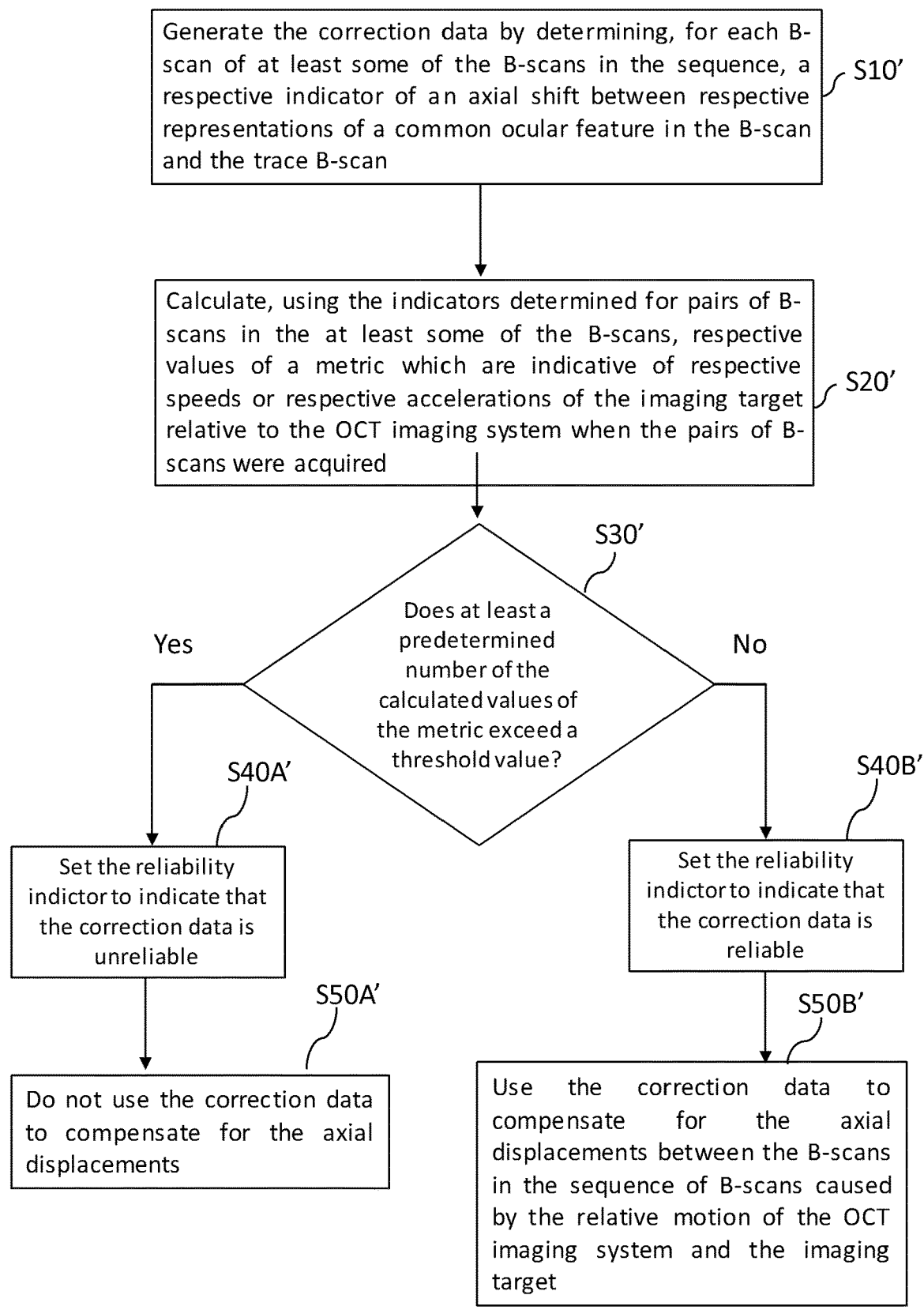
FIG. 11 is a flow diagram illustrating a method by which the data processing apparatus of the second example embodiment processes C-scan data to generate correction data for compensating axial displacements between B-scans, and a reliability indicator which indicates a reliability of the generated correction data.

FIG. 11 is a flow diagram illustrating a method by which the data processing apparatus 10' of FIG. 10 processes C-scan data comprising a sequence of B-scans to generate the correction data and the reliability indicator 5'. In step S10' of FIG. 11, the correction data generator module 2' generates the correction data by determining, for each B-scan of at least some of the B-scans in the sequence, a respective indicator of an axial shift between respective representations of a common ocular feature in the B-scan and the trace scan data.

Figure 12:
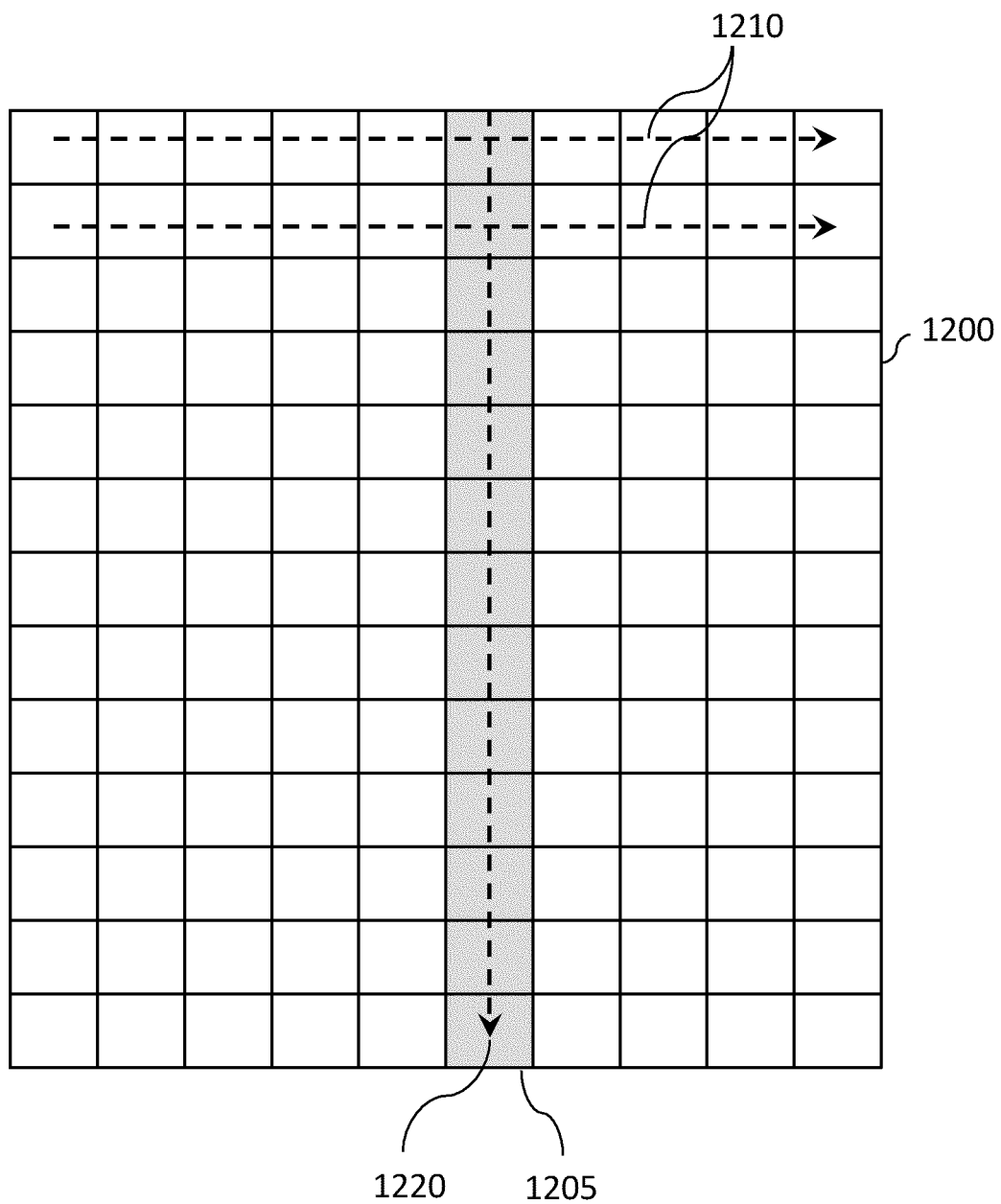
FIG. 12 is an illustration showing an example relationship between the locations of A-scans in a C-scan and A-scans of trace scan data.

FIG. 12 is an illustration showing the relationship between the location of A-scans in B-scans of a sequence of B-scans that form a C-scan, and A-scans from the trace scan data, according to a first example. In FIG. 12, the matrix 1200 represents a top-down view of a C-scan over all lateral positions of the imaging target covered by the C-scan. Each cell in matrix 1200 corresponds to an A-scan in the C-scan. Furthermore, each row of matrix 1200 correspond to a B-scan in the C-scan. The sequence of B-scans corresponding to the rows of matrix 1200 are acquired by performing OCT scans along a plurality of scan lines that extend along the imaging target 20. To illustrate this point, FIG. 12 shows a trace scan line 1220 superimposed on the matrix 1200, along which the OCT scan is performed to generate the corresponding trace scan data. In addition, in FIG. 12, each grey cell 1205 represents an A-scan of the trace scan data, which is superimposed on the C-scan represented by matrix 1200. The trace scan data in FIG. 12 is generated by performing an OCT scan along a trace scan line that extends across the imaging target 20.

As shown in FIG. 12, the trace scan line 1220 crosses the plurality of scan lines 1210, such that each B-scan in matrix 12000 (i.e. a row of the matrix 1200) has an A-scan that overlaps or crosses with a corresponding A-scan of the trace scan data. Therefore, A-scans of the B-scans and corresponding A-scans of the trace scan data may be used to determine the indicators described in step S10', based on a mapping that maps each A-scan in the C-scan to a correspondingly located A-scan in the trace scan data. The correction data generator module 2' may thus determine the indicator in step S10' by cross-correlating an A-scan in a B-scan of the sequence of B-scans, and a correspondingly located A-scan of the trace scan data. Alternatively, the correction data generator module 2' may use an appropriate feature identification algorithm to identify representations of a common feature in the A-scan of the B-scan and the correspondingly located A-scan of the trace scan data, before determining an offset (along an axial direction) between the respective representations of the common feature.

It should be noted however, that the trace scan line is not limited to being a straight line, as shown in FIG. 12, and may more generally extend across the imaging target 20 along any trajectory, provided that it crosses (or overlaps) with the scan lines which are scanned to generate the sequence of B-scans.

Figure 13:
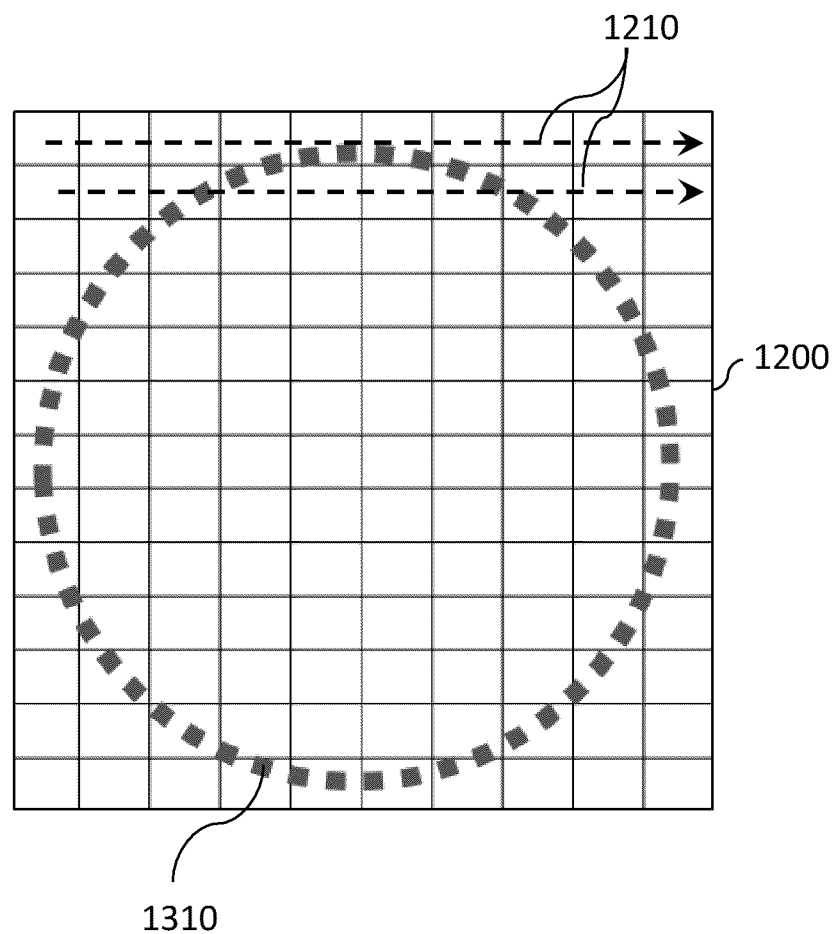
FIG. 13 is an illustration showing another example relationship between the locations of A-scans in a C-scan and A-scans of trace scan data.

FIG. 13 illustrates the relationship between the locations of A-scans in a C-scan, and A-scans that form the trace scan data, in another example where a circular trace scan is employed. The matrix 1200 represents a C-scan in the same way as explained in relation to FIG. 12. However, in the example of FIG. 13, the trace scan data comprises a plurality of A-scans 1310 that correspond to a plurality of lateral positions on the imaging target 20 that are scanned in a circular fashion by the OCT imaging light. In other words, in the present example, the trace scan line, along which the OCT imaging system 30 scans the OCT imaging light beam to generate the trace scan data, follows a circular trajectory along the surface of the imaging target 20. In addition, as shown in FIG. 13, depending on the density of the A-scans that form the trace scan data, multiple A-scans of the trace scan data may overlap with an A-scan of a B-scan in the sequence of B-scans forming the C-scan. In such cases, an indicator may be calculated for each of the multiple A-scans, and an average of the indicators obtained by the multiple A-scans may be calculated and used as the indicator for the B-scan, for example.

Referring again to FIG. 11, upon determining the correction data in step S10' of FIG. 11, the reliability data generator module 4' generates the reliability indicator 5' by performing steps S20', S30' and one of S40A' and S40B'. More specifically, at step S20', the correction data generator module 2' generates the reliability indicator 5' by calculating, using the indicators determined for pairs of B-scans 210, 220 in the at least some of the B-scans, respective values of a metric which are indicative of respective speeds or respective accelerations of the imaging target 20 relative to the OCT imaging system 30 when the pairs of B-scans 210, 220 were acquired.

The metric may, as in the present example embodiment, be a speed metric that is indicative of a speed (in the axial direction) of the imaging target 20 relative to the OCT imaging system 30. The speed metric may, as in the present example embodiment, be calculated using a pair of indicators from the plurality of indicators that are determined in step S10' of FIG. 11, the pair of indicators corresponding to two B-scans in the sequence of B-scans. In particular, a difference between the values of the two indicators, divided by the time between the acquisition of the two B-scans corresponding to the two indicators, is representative of the speed of the imaging target 20 relative to the OCT imaging system 30. The two indicators are not required to be indicators for two adjacent B-scans, and may instead be indicators corresponding to two non-adjacent B-scans in the sequence of B-scans.

In some example embodiments, instead of a speed metric, the metric calculated in step S20' of FIG. 4' may instead be an acceleration metric, which is indicative of the acceleration of the imaging target 20 relative to the OCT imaging system 30. The reliability indicator generation module 4' may calculate the acceleration metric by determining a first value indicative of a rate of axial shift of a common ocular feature in a first pair of B-scans, and a second value indicative of a rate of axial shift of a common ocular feature in a second pair of B-scans, wherein the first pair differs from the second pair by at least one B-scan. In the present example, the first value may be determined using a first pair of indicators corresponding to the first pair of B-scans in the plurality of indicators determined at step S10'. The first value may, for example, be calculated as a difference between the first pair of indicators. Similarly, the second value may be determined using a second pair of indicators corresponding to the second pair of B-scans in the plurality of indicators determined at step S10'. The second value may, for example, be calculated as a difference between the second pair of indicators. The reliability indicator generator module 4' may further evaluate the acceleration metric based on a difference between the first value and the second value. For example, for a first pair of B-scans captured at times T1 and T2, and having a determined rate of axial shift value of A1, and a second pair of B-scans captured at times T3 and T4 (occurring after T1 and T2) and having a determined rate of axial shift of A2, the acceleration metric may be calculated as:

$$\frac{A2 - A1}{0.5(T4 + T3) - 0.5(T2 + T1)}$$

However, it should be understood that the acceleration metric is not limited to the above form and may be calculated based on a difference between A2 and A2, and another measure of the temporal separation of the two pairs of B-scans, for example T3−T1 or T4−T2. When the metric is taken to be an acceleration metric in step S20', the threshold value set at step S30' may be set based on a maximum value of the acceleration that is considered realistic or physically possible.

In step S30' the reliability data generator module 4' further determines if at least a predetermined number of the calculated values of the metric exceed a threshold value. Step S30' is identical to step S30 of FIG. 1, with the only difference being that the threshold value, and the value of the predetermined number used in step S30', may be different from the corresponding features in step S30 of FIG. 1, owing to the difference in way by which the metric in S20' is calculated compared to the metric in step S20.

Returning to FIG. 11, in a case where at least the predetermined number of calculated values of the metric are determined to exceed the threshold value, the reliability indicator generator module 4' sets, at step S40A', the reliability indictor 5' to indicate that the correction data is unreliable. However, in a case where at least the predetermined number of calculated values of the metric are determined to not exceed the threshold value, reliability indicator generator module 4' sets the reliability indictor 5' to indicate that the correction data is reliable.

In some example embodiments, in the case where the reliability indicator 5' has been set to indicate that the correction data is reliable, the displacement compensation module 6' may use the correction data to compensate for the axial displacements between the B-scans in the sequence of B-scans caused by the relative motion of the OCT imaging system 30 and the imaging target 20, as shown in step S50B' of FIG. 11. On the other hand, in the case where the reliability indicator 5' has been set to indicate that the correction data is unreliable, the displacement compensation module 6' does not perform the aforementioned compensation for axial displacements between the B-scans using the correction data.

It should be understood that the data processing apparatus 10' of FIG. 10 differs from the apparatus of FIG. 1 in that, instead of generating the correction data by determining, for each pair of adjacent B-scans of a plurality of pairs of adjacent B-scans in the sequence, a respective indicator of an axial shift between respective representations of a common ocular feature in the adjacent B-scans, the correction data is instead generated by determining, for each B-scan of at least some of the B-scans in the sequence, a respective indicator of an axial shift between respective representations of a common ocular feature in the B-scan and the trace scan data. In this regard, all of the implementation details of the data processing apparatus 10 described above are also applicable to data processing apparatus 10'. For example, the process described with reference to FIG. 5 is also applicable to the data processing apparatus 10', with the only difference being that the first frequency component can be determined from a variation of the determined indicators with locations of the corresponding B-scans in the sequence in the present example embodiment. Furthermore, in cases where a polynomial is fitted to the indicators to determine the first frequency component, a different order polynomial may be select in the present example embodiment, given the different way by which the correction data generator module 2' generates its indicator compared to the correction data generator module 2 in FIG. 1.

For data processing apparatus 10', the determination of a second frequency component indicative of a curvature of imaging target 20, as described in relation to steps S310 to S330 of FIG. 7, need not be performed, since performing compensation based on correction data generated using trace scan data may allow the preservation of any curvature of the imaging target 20. This is because that curvature is captured by both the trace scan data as well as the sequence of B-scans, and any computed axial shifts between the trace scan data and the sequence of B-scans may only be the result of relative motion during scan acquisition, and spurious correlation results as discussed above. However, steps S440 to S470 of FIG. 8, and all examples and variations described above in relation to these steps, are also applicable to the data processing apparatus 10'. More specifically, for data processing apparatus 10', after determining a first frequency component by fitting an $n^{th}$ order polynomial to the variation indicators generated at step S10' of FIG. 11, data processing data apparatus 10' may generate the correction data by performing at least two iterations of a process comprising steps of:

(i) calculating a plurality of residual values, each residual value being calculated as a difference between an indicator in a variation of the determined indicators of axial shifts and a corresponding value of an $n^{th}$ order polynomial fitted to the variation of indictors;

(ii) determining whether the plurality of residual values comprise an outlier value which is higher than a first positive threshold value or lower than a first negative threshold value;

(iii) in case the plurality of residual values is determined to comprise the outlier value, removing the indicator corresponding to the outlier value from the variation of indicators to generate an updated variation of indicators and, in case the residual is determined not to comprise the outlier value, determining the nth order polynomial as the correction data and ending the process; and (iv) fitting the $n^{th}$ order polynomial to the updated variation of indicators.

Each residual value in the plurality of residual values is calculated in the first iteration of the process as a difference between an indicator in the corrected variation of the indicators and a corresponding value of the $n^{th}$ order polynomial fitted to the corrected variation of the indicators. Furthermore, each residual value in the plurality of residual values is calculated in each iteration of remaining one or more iterations of the process as a difference between an indicator in the updated variation of indicators generated in a previous iteration of the process and a corresponding value of the $n^{th}$ order polynomial fitted to the updated variation of indicators generated in the previous iteration of the process.

In addition, in the case where reliability indicator has been set to indicate that the correction data is reliable at S40B' of FIG. 11, the correction data generator module 2' may determine a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value. In a case where the determined number of residual values is smaller than a third threshold value, the displacement compensation module 6' may compensate for the axial displacements between the B-scans in the sequence of B-scans, by applying offsets based on the correction data to B-scans in the sequence of B-scans. However, in a case where the determined number of residual values is not smaller than a third threshold value, the displacement compensation module 6' may not compensate for the axial displacements between the B-scans in the sequence of B-scans.

The example aspects described here avoid limitations, specifically rooted in computer technology, relating to conventional OCT data processing, which can yield rendered volumetric OCT data displaying motion artefacts that are typically caused by involuntary movements of a subject during the acquisition of volumetric OCT data. These motion artefacts can adversely affect the accuracy of ocular feature identification and any subsequent diagnostic measurements, for example. By virtue of the example aspects described herein, correction data for compensating for axial displacements between B-scans in a sequence of B-scans forming a C-scan, which can be caused by a relative motion of the OCT imaging system and the imaging target, is generated. In particular, for each pair of adjacent B-scans in a sequence of B-scans, a respective indicator of an axial shift between respective representations of a common ocular feature in the adjacent B-scans is determined. Furthermore, a reliability indicator indicative of the reliability of the correction data is also generated. The reliability indicator is based on a metric indicative of a speed or an acceleration of the relative motion. In at least some embodiments, the correction data is only used to compensate axial displacements of the B-scans if the reliability indicator indicates the correction data is reliable. Accordingly, the processing of B-scans to compensate for axial displacement between B-scans can be improved, as only reliable correction data may be used to compensate for the axial displacements. In at least some embodiments, instead of generating the correction data by determining, for each pair of adjacent B-scans of a plurality of pairs of adjacent B-scans in the sequence, a respective indicator of an axial shift between respective representations of a common ocular feature in the adjacent B-scans, the correction data is instead generated by determining, for each B-scan of at least some of the B-scans in the sequence, a respective indicator of an axial shift between respective representations of a common ocular feature in the B-scan and the trace scan data. Furthermore, in at least some example embodiments, the residue of a polynomial fit to the determined variation of indicators is used to estimate a quality of the correction data, and thus determine whether compensation should be performed using the correction data. Also, by virtue of the foregoing capabilities of the example aspects described herein, which are rooted in computer technology, the example aspects described herein improve computers and computer processing/functionality, and also improve the field(s) of at least image processing, optical coherence tomography (OCT) and data processing, and the processing of OCT image data.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatuses described herein may be embodied in other specific forms without departing from the characteristics thereof. The foregoing embodiments are illustrative rather than limiting of the described systems and methods. Scope of the apparatuses described herein is thus indicated by the appended claims, rather than the foregoing description, and changes that come within the meaning and range of equivalence of the claims are embraced therein.

The invention claimed is:

1. A non-transitory, computer-readable storage medium storing computer program instructions which, when executed by a processor, cause the processor to execute a method of processing C-scan data comprising a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, and to further generate a reliability indicator which indicates a reliability of the generated correction data, the method comprising:
generating the correction data by determining, for each pair of adjacent B-scans of a plurality of pairs of adjacent B-scans in the sequence, a respective indicator of an axial shift between respective representations of a common ocular feature in the adjacent B-scans; and
generating the reliability indicator by:
calculating, using pairs of B-scans in the sequence of B-scans, respective values of a metric which are indicative of respective speeds or respective accelerations of the imaging target relative to the OCT imaging system when the pairs of B-scans were acquired;
determining if at least a predetermined number of the calculated values of the metric exceed a threshold value;
in a case where at least the predetermined number of calculated values of the metric are determined to exceed the threshold value, setting the reliability indictor to indicate that the correction data is unreliable; and
in a case where at least the predetermined number of calculated values of the metric are determined to not exceed the threshold value, setting the reliability indictor to indicate that the correction data is reliable.

2. The non-transitory, computer-readable storage medium according to claim 1, wherein the correction data is generated by determining, from a variation of the determined indicators with locations of the corresponding pairs of adjacent B-scans in the sequence, a first frequency component of the variation which is indicative of the relative motion of the OCT imaging system and the imaging target during acquisition of the B-scans by the OCT imaging system.

3. The non-transitory, computer-readable storage medium according to claim 2, wherein the imaging target has a curvature, and the method further comprises:
determining a second frequency component of the variation which is indicative of the curvature of the imaging target.

4. The non-transitory, computer-readable storage medium according to claim 3, wherein
the second frequency component is determined by fitting an $m^{th}$ order polynomial to the variation of the determined indicators, and
the first frequency component is determined by subtracting values of the $m^{th}$ order polynomial from the indicators in the variation of the determined indicators to generate a corrected variation of the indicators, and fitting an $n^{th}$ order polynomial to the corrected variation of the indicators, wherein m and n are integers and m is smaller than n.

5. The non-transitory, computer-readable storage medium according to claim 4, wherein the first frequency component is determined by further performing at least two iterations of a process comprising steps of:
(i) calculating a plurality of residual values, each residual value being calculated as a difference between an indicator in a variation of indicators and a corresponding value of an $n^{th}$ order polynomial;
(ii) determining whether the plurality of residual values comprise an outlier value which is higher than a first positive threshold value or lower than a first negative threshold value;
(iii) in case the plurality of residual values is determined to comprise the outlier value, removing the indicator corresponding to the outlier value from the variation of indicators to generate an updated variation of indicators and, in case the residual is determined not to comprise the outlier value, determining the $n^{th}$ order polynomial as the first frequency component and ending the process; and
(iv) fitting the $n^{th}$ order polynomial to the updated variation of indicators,
wherein each residual value in the plurality of residual values is calculated in the first iteration of the process as a difference between an indicator in the corrected variation of the indicators and a corresponding value of the $n^{th}$ order polynomial fitted to the corrected variation of the indicators, and
wherein each residual value in the plurality of residual values is calculated in each iteration of remaining one or more iterations of the process as a difference between an indicator in the updated variation of indicators generated in a previous iteration of the process and a corresponding value of the $n^{th}$ order polynomial fitted to the updated variation of indicators generated in the previous iteration of the process.

6. The non-transitory, computer-readable storage medium of claim 5, wherein the method further comprises, in the case where reliability indicator has been set to indicate that the correction data is reliable:
   determining a number of residual values in the plurality of residual values which have a magnitude larger than a second positive threshold value or smaller than a second negative threshold value, wherein the second positive threshold value is less than the first positive threshold value, and the second negative threshold value is greater than the first negative threshold value;
   in a case where the determined number of residual values is smaller than a third threshold value, compensating for the axial displacements between the B-scans in the sequence of B-scans, by applying offsets based on the first frequency component to B-scans in the sequence of B-scans; and
   in a case where the determined number of residual values is not smaller than a third threshold value, determining not to compensate for the axial displacements between the B-scans in the sequence of B-scans.

7. The non-transitory, computer-readable storage medium according to claim 1, wherein the respective indicator of the axial shift is determined for each pair of the adjacent B-scans by
   calculating a cross-correlation between the pair of adjacent B-scans and determining, as the indicator, an offset between the B-scans corresponding to a peak in the calculated cross-correlation, or
   identifying respective locations of the common ocular feature in the B-scans of the pair of adjacent B-scans, and determining a displacement between the identified locations along an axis of the B-scans that is representative of an axial direction of the imaging system.

8. The non-transitory, computer-readable storage medium according to claim 1, wherein the method further comprises, in the case where reliability indicator has been set to indicate that the correction data is reliable, using the correction data to compensate for the axial displacements between the B-scans in the sequence of B-scans caused by the relative motion of the OCT imaging system and the imaging target.

9. A data processing apparatus arranged to process C-scan data comprising a sequence of B-scans of an imaging target, which has been acquired by an optical coherence tomography, OCT, imaging system, to generate correction data for compensating for axial displacements between B-scans in the sequence of B-scans caused by a relative motion of the OCT imaging system and the imaging target that varies a distance therebetween during acquisition of the B-scans by the OCT imaging system, and to further generate a reliability indicator which indicates a reliability of the generated correction data, the apparatus comprising:
   a correction data generator module arranged to determine the correction data by determining, for each pair of adjacent B-scans of a plurality of pairs of adjacent B-scans in the sequence, a respective indicator of an axial shift between respective representations of a common ocular feature in the adjacent B-scans; and
   a reliability indicator generator module arranged to generate the reliability indicator by:
      calculating, using pairs of B-scans in the sequence of B-scans, respective values of a metric which are indicative of respective speeds or respective accelerations of the imaging target relative to the OCT imaging system when the pairs of B-scans were acquired;
      determining if at least a predetermined number of the calculated values of the metric exceed a threshold value;
      in a case where at least the predetermined number of calculated values of the metric are determined to exceed the threshold value, setting the reliability indictor to indicate that the correction data is unreliable; and
      in a case where at least the predetermined number of calculated values of the metric are determined to not exceed the threshold value, setting the reliability indictor to indicate that the correction data is reliable.

10. The data processing apparatus according to claim 9, wherein the correction data is generated by determining, from a variation of the determined indicators with locations of the corresponding pairs of adjacent B-scans in the sequence, a first frequency component of the variation that is indicative of the relative motion of the OCT imaging system and the imaging target during acquisition of the B-scans by the OCT imaging system.

11. The data processing apparatus according to claim 10, wherein the imaging target has a curvature, and a second frequency component of the variation is determined that is indicative of the curvature of the imaging target.

12. The data processing apparatus according to claim 11, wherein
   the second frequency component is determined by fitting an $m^{th}$ order polynomial to the variation of the determined indicators, and
   the first frequency component is determined by subtracting values of the $m^{th}$ order polynomial from the indicators in the variation of the determined indicators to generate a corrected variation of the indicators, and fitting an $n^{th}$ order polynomial to the corrected variation of the indicators, wherein m and n are integers and m is smaller than n.

13. The data processing apparatus according to claim 9, wherein the respective indicator of the axial shift is determined for each pair of the adjacent B-scans by
   calculating a cross-correlation between the pair of adjacent B-scans and determining, as the indicator, an offset between the B-scans corresponding to a peak in the calculated cross-correlation, or
   identifying respective locations of the common ocular feature in the B-scans of the pair of adjacent B-scans, and determining a displacement between the identified locations along an axis of the B-scans that is representative of an axial direction of the imaging system.

14. The data processing apparatus according to claim 9, wherein, in the case where reliability indicator has been set to indicate that the correction data is reliable, the correction data is used to compensate for the axial displacements between the B-scans in the sequence of B-scans caused by the relative motion of the OCT imaging system and the imaging target.

15. A system, comprising:
   at least one processor; and
   a memory storing instructions that, when executed by the at least one processor, causes the system to perform a set of operations, the set of operations comprising:
      obtaining C-scan data comprising a sequence of B-scans of an imaging target from an optical coherence tomography, OCT, imaging system;

generating correction data by determining, for each pair of adjacent B-scans of a plurality of pairs of adjacent B-scans in the sequence of B-scans, a respective indicator of an axial shift between respective representations of a common ocular feature in the adjacent B-scans; and generating a reliability indicator indicative of a reliability of the generated correction data by:

calculating, using pairs of B-scans in the sequence of B-scans, respective values of a metric which are indicative of respective speeds or respective accelerations of the imaging target relative to the OCT imaging system when the pairs of B-scans were acquired;

determining if at least a predetermined number of the calculated values of the metric exceed a threshold value;

in a case where at least the predetermined number of calculated values of the metric are determined to exceed the threshold value, setting the reliability indictor to indicate that the correction data is unreliable; and in a case where at least the predetermined number of calculated values of the metric are determined to not exceed the threshold value, setting the reliability indictor to indicate that the correction data is reliable.

16. The system of claim 15, wherein the correction data is generated by determining, from a variation of the determined indicators with locations of the corresponding pairs of adjacent B-scans in the sequence, a first frequency component of the variation which is indicative of the relative motion of the OCT imaging system and the imaging target during acquisition of the B-scans by the OCT imaging system.

17. The system of claim 16, wherein the imaging target has a curvature, and the set of operations further comprises:

determining a second frequency component of the variation which is indicative of the curvature of the imaging target.

18. The system of claim 15, wherein the respective indicator of the axial shift is determined for each pair of the adjacent B-scans by calculating a cross-correlation between the pair of adjacent B-scans and determining, as the indicator, an offset between the B-scans corresponding to a peak in the calculated cross-correlation, or identifying respective locations of the common ocular feature in the B-scans of the pair of adjacent B-scans, and determining a displacement between the identified locations along an axis of the B-scans that is representative of an axial direction of the imaging system.

19. A method of generating correction data and a corresponding reliability indicator for C-scan data of an optical coherence tomography, OCT, imaging system, the method comprising:

obtaining the C-scan data comprising a sequence of B-scans of an imaging target from the OCT imaging system;

generating the correction data by determining, for each pair of adjacent B-scans of a plurality of pairs of adjacent B-scans in the sequence of B-scans, a respective indicator of an axial shift between respective representations of a common ocular feature in the adjacent B-scans; and generating the reliability indicator indicative of a reliability of the generated correction data by:

calculating, using pairs of B-scans in the sequence of B-scans, respective values of a metric which are indicative of respective speeds or respective accelerations of the imaging target relative to the OCT imaging system when the pairs of B-scans were acquired;

determining if at least a predetermined number of the calculated values of the metric exceed a threshold value;

in a case where at least the predetermined number of calculated values of the metric are determined to exceed the threshold value, setting the reliability indictor to indicate that the correction data is unreliable; and in a case where at least the predetermined number of calculated values of the metric are determined to not exceed the threshold value, setting the reliability indictor to indicate that the correction data is reliable.

20. The method of claim 19, wherein the respective indicator of the axial shift is determined for each pair of the adjacent B-scans by calculating a cross-correlation between the pair of adjacent B-scans and determining, as the indicator, an offset between the B-scans corresponding to a peak in the calculated cross-correlation, or identifying respective locations of the common ocular feature in the B-scans of the pair of adjacent B-scans, and determining a displacement between the identified locations along an axis of the B-scans that is representative of an axial direction of the imaging system.

* * * * *